(12) United States Patent
Shekhar et al.

(10) Patent No.: US 6,828,111 B2
(45) Date of Patent: Dec. 7, 2004

(54) THREE-DIMENSIONAL IN VITRO MODEL OF HUMAN PRENEOPLASTIC BREAST DISEASE

(75) Inventors: Malathy P. V. Shekhar, Northville, MI (US); Larry Tait, Dewitt, MI (US)

(73) Assignee: Wayne State University, Detroit, MI (US)

( * ) Notice: Subject to any disclaimer, the term of this patent is extended or adjusted under 35 U.S.C. 154(b) by 22 days.

(21) Appl. No.: 09/759,365

(22) Filed: Jan. 16, 2001

(65) Prior Publication Data

US 2001/0055804 A1 Dec. 27, 2001

Related U.S. Application Data

(60) Provisional application No. 60/175,962, filed on Jan. 13, 2000.

(51) Int. Cl.[7] .................. G01N 33/53; G01N 33/567
(52) U.S. Cl. ...................................... 435/7.1; 435/7.21
(58) Field of Search .............................. 435/7.1, 7.21

(56) References Cited

U.S. PATENT DOCUMENTS

| | | |
|---|---|---|
| 4,423,145 A | 12/1983 | Stampfer et al. |
| 4,439,521 A | 3/1984 | Archer et al. |
| 5,032,508 A | 7/1991 | Naughton et al. |
| 5,059,586 A | 10/1991 | Collier et al. |
| 5,153,132 A | 10/1992 | Goodwin et al. |
| 5,308,764 A | 5/1994 | Goodwin et al. |
| 5,496,722 A | 3/1996 | Goodwin et al. |
| 5,814,511 A | 9/1998 | Chang et al. |

OTHER PUBLICATIONS

Ma et al. (IOVS Jul. 1999 40(8):1822–1828).*
Gura Science Nov. 1997 278:1041–1042.*
Evans et al Q J. Med 1999; 92:299–307.*
Saiag, P. et al., Science, 230: 669–672, 1985.
Tait, L et al., Cancer Res., 50: 6087–6094, 1990.
Basolo, F. et al., "Transformation of Human Breast Epithelial Cells By c–Ha–ras Oncogene", *Mol. Carcinogen.* 4:25–35, 1991.
Miller, F.R. et al., "Xenograft Model of Progressive Human Proliferative Breast Disease", *J. Nat. Cancer Inst.,* 85:1725–1732, 1993.
Schor, A.M. et al., "Phenotypic Heterogeneity In Breast Fibroblasts: Functional Anomaly in Fibroblasts From Histologically Normal Tissue Adjacent to Carcinoma", *Int. J Cancer,* 59: 25–32, 1994.
Boudreau, N. et al., "Supression of ICE and Apoptosis In Mammary Epithelial Cells By Extracellular Matrix", Science 267:891–893, 1995.
Shekhar, P.V.M. et al., "Environmental Estrogen Stimulation of Growth and Estrogen Receptor Function in Preneoplastic and Cancerous Human Breast Cell Lines", J. Natl. Cancer Inst., 89:1774–1782, 1997.
Shekhar, P.V.M. et al., "Direct Action of Estrogen on Sequence of Progresison of Human Preneoplastic Breast Disease", Int. J. Oncology, 13:907–915, 1998.
Shekhar, P.V.M. et al., "Transcriptional Activation of Functional Endogenous Estrogen Receptor Gene Expression in MCF10AT Cells: A Model For Early Breast Cancer", Amer. J. Pathol., 152:1129–1132, 1998.
Moinfar, F. et al., "Concurrent and Independent Genetic Alterations in the Stormal and Epithelial Cells of Mammary Carbinoa: Implications for Tumorigenesis", Cancer Res., 60: 2562–2566, 2000.
Heppner et al., "Nontransgenic Models of Breast Cancer", Breast Cancer Res. 2:331–334 (2000).
Barcellos–Hoff MH , "Three Down and Counting: The Transformation of Human Mammary Cells from Normal to Malignant in Three Steps", *Trends Mol Med* Apr.;7(4):142–3, 2001.

* cited by examiner

*Primary Examiner*—Gary Nickol
*Assistant Examiner*—Christopher Yaen
(74) *Attorney, Agent, or Firm*—Venable LLP; Sandy Livnat

(57) ABSTRACT

A three-dimensional in vitro culture system comprising breast epithelial cells, endothelial cells and breast fibroblasts supports growth and functional differentiation of preneoplastic breast epithelial cells and endothelial cells and recapitulates estrogen induced in vivo effects on angiogenesis and proliferative potential of breast epithelial tissue. This model permits the generation of functional vascular networks and local proliferative ductal alveolar outgrowths with invasive potential. Both these processes are augmented by estrogen. This culture model is used to evaluate agents for their effects, whether stimulatory or inhibitory, on preneoplastic breast disease and its progression to cancer.

33 Claims, 15 Drawing Sheets

THREE-DIMENSIONAL IN VITRO MODEL OF HUMAN PRENEOPLASTIC BREAST DISEASE

CROSS-REFERENCE TO RELATED APPLICATIONS

This application claims benefit of U.S. Provisional Application 60/175,962, filed Jan. 13, 2000, which is incorporated herein by reference.

STATEMENT OF RIGHTS TO INVENTIONS MADE UNDER FEDERALLY SPONSORED RESEARCH

This invention was funded in part by a grant from the United States Army Medical Research and Material Command and from the National Cancer Institute, which provides to the United States government certain rights in this invention.

BACKGROUND OF THE INVENTION

1. Field of the Invention

The present invention in the field of biology and medicine relates to a cell culture model system that mimics human preneoplastic breast disease and uses thereof in screening agents that inhibit development of this disease and its progression to breast cancer.

2. Description of the Background Art

Reciprocal cellular interactions between epithelial and stromal cells have been demonstrated as a key determinant in the morphogenesis, proliferation and cyto-differentiation of both endocrine and non-endocrine target organs (I. Hom, Y. K. et al., Endocrinology, 139: 913–921, 1998; Donjacour, A. A. et al., Cancer Treatment Res., 53: 335–364, 1991; Cunha, G. R. et al., Cell Differ., 17:137–148, 1985). Carcinomas of the breast are composed of not only tumor epithelial cells but also of infiltrating endothelial cells ("EC's"), fibroblasts, macrophages and lymphocytes (Gregoire, M. et al., Cancer Metast. Rev., 14: 339–350, 1995). The stroma provides vascular supply and specific soluble and extracellular matrix (ECM) molecules that are required for tumor growth and progression (Hanahan, D. et al., Cell, 86: 353–364, 1996). Several lines of evidence indicate that stromal cells play a central role via ECM remodeling in tumor invasion and dissemination (Camps, J. L. et al., Proc. Natl. Acad., Sci. USA, 87: 75–79, 1990; Picard, O., et al. Cancer Res., 46: 3290–3294, 1986; Grey, A. M. et al., Proc. Natl. Acad. Sci. USA, 86: 2438–2442, 1989). However, a recent report has shown that stromal alteration(s) precede the malignant conversion of tumor cells (Moinfar, F. et al., Cancer Res., 60: 2562–2566, 2000).

Although there is experimental evidence supporting the involvement of angiogenesis in pathogenesis of breast cancer, the influence of functional interactions between human breast epithelial cells (also referred to as mammary epithelial cells) and endothelial cells have not been defined. Analysis of such cell interactions requires a culture/assay system that permits growth and differentiation of both epithelial cells and endothelial cells.

The present invention provides such a system and describes its utility as a model for studying the progress of preneoplastic lesions to cancer and for testing the activity of agents that can inhibit this process.

Growth and formation of capillary blood vessels or neovascularization is an essential component of solid tumor growth (Folkman, J. et al., Int. Rev. Exp. Pathol. 16: 207, 1976; Gimbrone, M. A. Jr et al., J. Natl. Cancer Inst., 52: 413, 1974). Any increase in the size of the tumor cell population must be preceded by an increase in new capillaries that converge upon the tumor; such angiogenesis has been directly correlated with tumor growth and metastasis (Folkman, J, J. Nat'l Canc Inst 82:4–6, 1990). Tumor cell products and products of various non-neoplastic mediator systems have been implicated in this vasoproliferative response (Gimbrone et al., supra; Auerbach, R., In: E. Pick (ed), Lymphokines. Vol 4, pp. 69–84, New York: Academic Press, 1981). Several growth factors, cytokines, molecules of the extracellular matrix (ECM) or physical conditions induce or regulate endothelial cell growth and/or migration in vitro (Klagsbrun, M. et al., Ann. Rev. Physiol. 53:217–239, 1991). These include several well characterized polypeptide growth factors, proteolytic enzymes, interferon, cyclic nucleotides, prostaglandins, heparin, lowered oxygen tension, histamine and other vasoactive amines, and several low molecular weight endothelial mitogens and chemotactic factors (Klagsbrun et al., supra).

Vascular endothelial growth factor (Ferrara, N. et al., Biochem. Biophys. Res. Commun., 161:851–858, 1989) or vascular permeability factor (Connolly, D. T. et al., J. Biol. Chem., 264:20017–20024, 1989) (abbreviated VEGF/PF or VEGF) is an endothelial cell-specific mitogen that mediates physiological and pathological neovascularization (Leung, D. W. et al., Science 246:1306–1309, 1989). VEGF acts as a survival factor, preventing the apoptotic death of microvascular endothelial cells (Alon, T. et al., Nat. Med., 1:1024–1028, 1995, 1995; Watanabe, Y. et al., Exp. Cell. Res., 233:340–349, 1997). The human VEGF gene encodes a dimeric glycoprotein comprising four possible monomers as a result of differential splicing of eight exons that make up the gene product. The four VEGF subtypes are 121-, 165-, 189-, and 206-amino acids in length (Neufeld, G. et al., FASEB J., 13:9–22, 1999). The smaller forms are secreted whereas $VEGF_{189}$ and $VEGF_{206}$ are bound to heparan proteoglycans and thus retained close to the membrane of producing cells. Three receptors for VEGF have been described:

VEGFR-1 (=Flt-1) binds VEGF;

VEGFR-2 (=Flk-1/KDR) binds VEGF; and

VEGFR-3 (=Flt-4) appears to be specific for VEGF-C (Neufeld et al., supra).

Expression of Flk-1/KDR is confined to endothelial cells, accounting for the selective nature of VEGF-induced mitogenesis (Neufeld, supra). VEGF is expressed at high levels in a wide range of tumors and tumor cell lines (Berse, B. et al., Mol. Biol. Cell, 3:211–220, 1992) and is believed to be a key mediator of (1) tumor angiogenesis (Connolly, D. T. et al., J. Clin. Invest., 84:1470–1477, 1989; Kim, K. J. et al., Nature (London), 362:841–844, 1993; Plate, K. H. et al., Nature (London), 359:845–848, 1992) and (2) the high blood vessel permeability characteristic of tumors (Senge, D. R. et al., Science 219:983–985, 1983; Yeo, K. T. et al., Cancer Res., 53:2912–2918, 1983). Expression of VEGF in the uterus was rapidly and strongly stimulated by estrogen (Cullinan-Bove, K. et al., Endocrinology, 133:829–837, 1993), suggesting that VEGF mediates the normal, estrogen-induced increase in vascular permeability and blood vessel growth in the uterus. Similarly, expression of VEGF is rapidly induced by 17 β-estradiol ($E_2$) in dimethylbenzanthracene (DMBA)-induced estrogen-dependent mammary tumors (Nakamura, J. et al., Endocrinology, 137:5589–5596, 1996).

Using the MCF10AT1 xenograft model for human proliferative breast disease, the present inventors and their colleagues previously demonstrated that $E_2$ exerts a growth promoting effect on benign or premalignant ductal epithelium by enhancing the speed of transformation from simple/mild hyperplasia (grades 0/1) to atypical hyperplasia (grade 3) and ductal carcinoma in situ (grade 4) (Shekhar, P. V. M. et al., Amer. J. Pathol., 152:1129–1132, 1998). Table 1, below, summarizes the criteria for grading proliferative breast lesions (from Dawson, P. J. et al., Am. J. Pathol., 148:313–319, 1996).

Much of this growth promoting effect appeared to arise from effects of $E_2$ on angiogenesis since lesions from unsupplemented animals were either simple or hyperplastic without atypia and lack angiogenesis. The dramatic increase in growth and advanced histological grades of progression concomitant with its remarkable effect on angiogenesis suggested to the present inventors that one of the mechanisms by which $E_2$ acts as a breast cancer promoter could be through its effect on expression of angiogenesis-regulating factors.

The extracellular matrix (ECM) acts locally to modulate the responsiveness of endothelial cells and mammary epithelial cells to external factors. Besides providing a scaffolding during capillary morphogenesis, the ECM, by virtue of its ability to mediate both biochemical and biomechanical signaling events, exerts complex local controls on the functions of endothelial cells (Polverini, P. J., Eur. J. Cancer, 32A:2430–2437, 1996). For example, the ECM controls growth, differentiation and apoptosis of normal murine and human breast epithelial cells (Barcellos-Hoff, M. H. et al., Development, 105:223–235, 1989; Boudreau, N. et al., Science 267:891–893, 1995).

Collagenolytic degradation of endothelial and parenchymal basement membranes is an essential step in the process of tumor invasion and angiogenesis (Liotta, L. A. et al., Cell, 64:327–336, 1991). Proteolysis and interruption of the basement membrane and ECM require the activation of specialized matrix metalloproteinases (MMPs), the type IV collagenases or gelatinases that degrade basement membrane collagens type IV and V (Liotta, L. A. et al., Nature 284:67–68, 1980). Two MMP species have been cloned and sequenced:

(1) the 72 kDa enzyme known as MMP-2 and gelatinase A) and (2) the 92 kDa enzyme known as MMP-9 and gelatinase B (Liotta et al., supra, Liotta, L. A. et al., Biochemistry, 20:100–104, 1981; Wilhelm, S. M. et al., J. Biol. Chem., 264:17213–21, 1989). MMP-2 and MMP-9 are secreted as latent proenzymes; activation requires removal of an 80 residue and 87 residue N-terminal domain, respectively (Stetler-Stevenson, W. G. et al., J. Biol. Chem., 264:1353–6, 1989; Collier, I. E. et al., J. Biol. Chem., 263:6579–87, 1988).

TABLE 1

Criteria for Grading of Proliferative Breast Lesions (Preneoplasia)

| Grade | Classification | Description |
| --- | --- | --- |
| 0 | Simple Epithelium | Small ducts |
| | | Single layer of luminal epithelium* |
| | | No nuclear enlargement |
| | | No nucleoli or mitoses |
| 1 | Mild Hyperplasia | Small ducts |
| | | Two or more layers of epithelial cells* |
| | | No significant bridging |
| | | Variable nuclear contours |
| 2 | Moderate hyperplasia | Mildly distended ducts |
| | | Four or more layers of epithelial cells* |
| | | Irregular papillary proliferation |
| | | Bridging by non-uniform cells |
| | | Irregularly shaped lumens |
| | | No solidly filled spaces |
| | | Indistinct cell boundaries |
| | | Variable nuclear contours |
| | | Bland chromatin, small nucleoli |
| 3 | Atypical hyperplasia | Grossly distended ducts |
| | | Regular microcapillary configuration |
| | | Marked cellular proliferation often forming luminal mass |
| | | Some regularity (roundness) of spaces |
| | | Some loss of polarity |
| | | Cells become monotonous |
| | | Tendency to clear cytoplasm with distinct borders |
| | | Enlarged, nonround hyperchromatic nuclei |
| | | Small nucleoli, occasional mitoses |
| 4 | Carcinoma in situ | Distended ducts filled with uniform cells |
| | | Rigid intraluminal bridges |
| | | Occasional central necrosis |
| | | Distinct cell boundaries |
| | | Uniform round, hyperchromatic, enlarged nuclei |
| | | Tendency to clear cytoplasm with distinct borders |
| | | Enlarged, nonround hyperchromatic nuclei |
| | | Prominent nucleoli, frequent mitoses |
| 5 | Invasive carcinoma | Glandular, squamous o, or undifferentiated |

*Because of the inconspicuous nature of the myoepithelial cells in many of the specimens, they were not considered as a layer Stampfer et al., U.S. Pat. No. 4,423,145 describes growth medium and conditions for culturing human mammary epithelial cells. The document discloses that clonal growth of these cells is improved by using a skin fibroblast feeder layer. Although this is an example of a two cell heterotypic culture, it differs from the present invention in numerous significant ways, in that no mention is made of co-culture with endothelial cells. Moreover, in contrast to the present invention fibroblasts are used merely as a feeder layer to allow better proliferation of epithelial cells that are plated at low density for cloning. Under these conditions, although the epithelial cells proliferate better, they do not undergo any morphological conversions such as those described in the present invention. Furthermore, skin fibroblasts, which are not part of the present invention, are the only fibroblast type disclosed.

Naughton et al., U.S. Pat. No. 5,032,508 discloses a 3D matrix and its use as the framework for a 3D, multi-layer cell culture system which is said to be an improvement over previously known tissue culture systems wherein cells grew in a monolayer. In this approach, a solid phase 3D support material that allows cells to attach and to grow in more than one layer is inoculated with stromal cells, comprising fibroblasts with or without additional cells. This stromal matrix (which can be generic or tissue-specific) is then inoculated with parenchymal or tissue cells which grow the 3D stromal support in multiple layers, forming a cellular matrix. This matrix system was said to be a closer model of physiologic in vivo conditions than were previously described monolayer tissue culture systems. The 3D cell culture system was disclosed as being applicable to proliferation of different types of cells and the formation of a number of different tissues. The document specifically listed and exemplified bone marrow, skin, liver, pancreas, kidney, adrenal and neurologic tissue. This system was said to be useful for in vitro cytotoxicity testing and screening compounds including growth/regulatory factors, pharmaceutical agents. This document does not disclose breast epithelial cells, and only mentions mucosal epithelium (model systems to study herpesvirus or papilloma virus infection) or dermal epithelium in modeling skin. The only mention of "breast" is in the background where the document refers to 3D collagen gels for culturing breast epithelium (Yang et al., 1981, Cancer Res. 41:1021–1027). Breast tissue, breast epithelial cells, breast fibroblasts or breast disease are never mentioned in the description of the invention. Endothelial cells are discussed only as one type of stromal cell, e.g., in vascular endothelium (for modeling blood brain barrier in vitro) bile duct endothelium (liver culture) or in bone marrow cultures.

Jones et al., U.S. Pat. No. 5,935,853, discloses the discovery that the MCF-10A cell line, an immortalized human mammary epithelial cell line, produces an ECM which is capable of stimulating hemidesmosome formation in unrelated epithelial cells contacted with the matrix. The MCF-10A cell line produces both a deposited (insoluble) and a similar secreted (soluble) matrix. The document discloses a method of growing epithelial cells by contacting the cells with the ECM deposited or secreted MCF-10A cells.

Chang et al., U.S. Pat. No. 5,814,511 describes a substantially purified human breast epithelial cell (Type I HBEC) and a method of obtaining these epithelial cells comprising the steps of: a) development of a mixture of human breast epithelial cells from reduction mammoplasty tissues using the MSU-1 medium; b) eliminating stromal fibroblasts by a trypsin (0.002%) and ethylenediamine tetraacetic acid (0.02%) solution; c) separating Type I HBEC from Type II HBEC which attach on culture dishes earlier by collecting Type I HBEC that remain in suspension after trypsinization and prolonged incubation; d) the continuing culture of these cells in MSU-1 medium supplemented with fetal bovine serum, which inhibits the growth of Type II HBEC while promoting the growth of Type I HBEC, gives rise to Type I HBEC. Described also is a new defined medium (the MSU-1 medium) which supports the growth of both Type I and Type II human breast epithelial cells.

Goodwin et al., U.S. Pat. Nos. 5,308,764 and 5,496,722, disclose 3D cell cultures comprising aggregates of normal mammalian cells (for each of the three major tissue groups). The culture aggregates were produced under microgravity culture conditions (microgravity or simulated microgravity created in unit gravity by controlling the horizontal rotation of a culture vessel containing normal mammalian cells). These cell aggregates exhibited 3D tissue growth and functional interrelationship by cell to cell contact. Functional cells with normal morphology were produced for organ, structural and blood producing tissues. The process for producing the normal mammalian tissue was said to be is particularly unique in that it could produce normal tissue of 2 mm and larger. The starting cell inoculum was predominantly normal differentiated epithelial cells and predominantly normal differentiated mesenchymal cells (disassociated prior to introduction). The epithelial and mesenchymal cells were introduced in a vessel with a culture matrix preferably of generally spherical microcarriers. Tissue engineering was achieved by selected introduction of the mesenchymal cells and culture matrix for a preselected culture period prior to transfer of epithelial cells to the culture vessel.

Goodwin et al., U.S. Pat. No. 5,153,132 discloses a method for culturing at least two distinct originating types of mammalian cells such as stromal cells and epithelial cells. The method, which requires a constantly and controllably rotating culture chamber and the presence of microcarriers (cell attachment substrates), resulted in the in vitro generation of multi-cellular, 3D, differentiated, organized living tissues.

Collier et al., U.S. Pat. No. 5,059,586 disclosed enhancement of the growth of milk-producing mammary parenchyma in a mammal by intramammary infusion a substance that was mitogenic for mammary epithelial cells in the mammal.

Archer et al., U.S. Pat. No. 4,439,521, disclosed a method for producing 3_D pancreatic islet-like structures having histology and functionality (insulin-production) corresponding to those of fetal pancreatic islets and islets from adult animals maintained in culture. The method involved culturing, attached to a substrate, isolated natural pancreatic islets, pancreatic duct pieces, cell clusters consisting of mildly digested pieces of pancreas, cell tissues obtained as by-products of the culturing methods, or previously-produced islet-like structures. The formation of the structures occurs over about 5–17 weeks in culture. This document does not disclose the 3D culture of any other types of cells.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

Since commitment to the morphogenetic and differentiation programs requires the establishment of intercellular communication between breast stromal and epithelial cells, the present inventors have established a novel three dimensional ("3D") cell-cell interaction model to study the molecular and cellular basis of epithelial-fibroblast-endothelial cell interactions.

The present model/assay system recapitulates in vitro the in vivo processes that lead to breast cancer development and progression from preneoplastic tissue. This model is the first that allows demonstration in vitro the de novo development and neoplastic conversion of functional alveolar units. Advantages of this model include the fact that it requires only about 7 days for alveolar morphogenesis to occur compared to 8–10 weeks in vivo. This permits the use of this system for relatively high throughput drug screening (see below).

As described below, this system has been used to compare the abilities of specific mesenchymal cell types and human umbilical vein endothelial cells (HUVEC) to induce three dimensional morphogenesis and growth of normal-behaving MCF10A and preneoplastic MCF10AT1-EIII8 human breast epithelial cells. The present invention demonstrates not only a requirement for breast-specific fibroblasts but also shows the dominant manner by which normal breast fibroblasts (obtained during reduction mammoplasty) and tumor-derived breast fibroblasts suppress or induce, respectively, growth and ductal-alveolar morphogenesis of MCF10A and MCF10AT1-EIII8 breast epithelial cells.

In this model, preneoplastic human breast epithelial cells interact with two major stromal components, endothelial cells and fibroblasts, on a reconstituted basement membrane and undergo alveolar morphogenesis, a critical step in breast tissue morphogenesis. The assay system shows that alveolar morphogenesis of human breast epithelial cells occurs when the preneoplastic epithelial cells interact with either endothelial cells or breast fibroblasts. However, neoplastic conversion of alveolar functional units occurs only when endothelial cells are present in epithelial-fibroblast co-cultures. The present inventors have shown for the first time using this model the biological requirements and/or contribution from epithelial cells and stromal components for formation of functional ductal lobular units, and processes that allow neoplastic conversion.

Thus, the present invention is directed to a 3D in vitro culture system that serves as a model for the development and progression of preneoplastic breast disease and is therefore useful for screening therapeutic agent that prevent or inhibit breast cancer development, the model system comprising a co-culture of
(a) preneoplastic breast epithelial cells; (b) endothelial cells; and (c) breast fibroblasts on a reconstituted basement membrane in the presence of medium containing (i) effective concentrations of growth factors and additives that act on the epithelial and endothelial cells, and (ii) effective concentrations of an estrogen such that the cells undergo morphogenesis that results in the formation of s multicellular 3D network of branching ductal alveolar units in culture within about 3–7 days. The above cells are preferably human cells.

In this culture system, the growth factors acting on endothelial cells preferably comprise epidermal growth factor (EGF), basic fibroblast growth factor (bFGF) and fibronectin, and the growth factors and additives acting on the epithelial cells preferably comprise cholera toxin, insulin, EGF and hydrocortisone.

In the above culture system, the epithelial cells are preferably transformed by T24 Ha-ras cells or are cells derived therefrom by xenotransplantation in nude mice. Preferred lines of epithelial cells are MCF10AT1 or MCF10AT1-EIII8 ("EIII8") cells, in particular EIII8.

In the above culture system, the endothelial cells are preferably human umbilical vein endothelial cells (HUVEC and the reconstituted basement membrane is preferably Matrigel®.

A preferred medium for the above culture system is DMEM-F12 medium, which more preferably is supplemented with 0.1 $\mu$g/ml cholera toxin, 10 $\mu$g/ml insulin, 0.5 $\mu$g/ml hydrocortisone, 0.02 $\mu$g/ml EGF.

In the above culture system 1 wherein the preferred estrogen is estradiol at a concentration between about 1 and 10 nM.

The epithelial cells in the above culture system preferably produce mucin and express cytokeratins and proliferating cellular nuclear antigen.

In the above culture system, as a result of secretion by the cells, the medium preferably contains measurable concentrations or activities of one or more of interleukin-8, matrix metalloproteinase-2 and VEGF.

In another embodiment, the present invention provides a method for assaying a test agent for its activity of preventing or inhibiting the development or progression of preneoplastic breast disease. The method comprises:

(a) adding the test agent to a culture that comprises the model system of claim 1 for an interval sufficient for the agent to act upon the preneoplastic breast epithelial cells, the endothelial cells or the fibroblasts
(b) to a parallel culture, adding a negative control agent for the interval, which negative control agent does not prevent or inhibit the progression,
(c) examining the cultures of (a) and (b), above, for
   i. formation of the branching ductal alveolar units by morphology; or
   ii. proliferation of cells; or
   iii. the presence in the culture medium of one or more secreted products of the cells wherein prevention or inhibition of the unit formation, the proliferation or generation of the secreted products in cultures of (a) compared to (b), is indicative that the agent has the activity.

The above method may also include the addition of a third parallel culture group which is a positive control agent known to inhibit the formation, proliferation or presence of secreted products.

In one embodiment of the above method, the assaying comprises, in step (c), examining the cultures morphologically for the branching ductal alveolar units. Another embodiment measures the proliferation of cells, preferably by a colorimetric assay. Yet another embodiment measures the presence or amount of the secreted products in the culture medium, for example, by assaying immunoreactivity in an immunoassay or by biological activity in a bioassay. Examples of such secreted products included growth or angiogenic factors, e.g., VEGF.

The secreted factor may be assayed for its stimulation of proliferation or of endothelial tube formation (thought to be related to angiogenesis) in culture.

In one embodiment, the test agent inhibits proteolytic enzymes that are required for invasion and transformation to malignancy. Thus, the secreted product may be a matrix metalloproteinase that is assayed by enzymatic activity on a specific substrate.

The test agent may be one that induces terminal differentiation of breast epithelial cells and thereby inhibits neoplastic conversion.

The present invention also is directed to a method for testing an agent for its activity as an endothelial cell-specific or epithelial cell-specific factor active in promoting ductal-alveolar morphogenesis, angiogenesis and progression of preneoplastic breast epithelial cells to a malignant phenotype, comprising:

(a) adding the agent to a culture that comprises the model system of claim 1 for an interval sufficient for the agent to act upon the preneoplastic breast epithelial cells or the endothelial cells;
(b) to a parallel culture, adding a negative control agent for the interval, which negative control agent does not promote ductal-alveolar morphogenesis, angiogenesis or progression of preneoplastic breast epithelial cells to a malignant phenotype;
(c) examining the cultures of (a) and (b), above, for
   i. formation of the branching ductal alveolar units by morphology; or
   ii. cellular changes corresponding to angiogenesis; or
   iii. progression of preneoplastic breast epithelial cells to a malignant phenotype, wherein promoting of the unit formation, the cellular changes corresponding to angiogenesis, or the progression in cultures of (a) compared to (b), is indicative that the agent has the activity.

In the above method, it is useful to add a third parallel culture group which is a positive control agent known to promote ductal-alveolar morphogenesis, angiogenesis or progression of preneoplastic breast epithelial cells to a malignant phenotype.

BRIEF DESCRIPTION OF THE DRAWINGS

FIG. 8A: $VEGF_{165}$ levels were analyzed in culture media of 5 day-old homotypic (EIII8 or MCF10A), heterotypic (EIII8-HUVEC or MCF10A-HUVEC) cultures, or in HUVEC cells at 48 h of culture. FIG. 8B: Levels of $VEGF_{165}$ secreted into culture media from EIII8-HUVEC co-cultures were analyzed on days 1, 5 and 10 of culture. Culture media were collected at indicated times from cultures treated with vehicle (0.01% ethanol, v/v), 1 nM $E_2$ or a combination of 1 nM $E_2$ and a 100-fold molar excess of ICI 182,780.

FIG. 8C: steady-state levels of Flk-1 and ER, or IL-8 were analyzed in matrix and corresponding culture media, respectively, from HUVEC cultures on day 2 (lane 1), MCF10A-HUVEC (lanes 2 and 3), or EIII8-HUVEC (lanes 4–9) cultures on days 5 (lane 2, and lanes 4–6) and 10 (lane 3, and lanes 7–9). Cultures were treated with vehicle (lanes 1–4 and 7), 1 nM $E_2$ (lanes 5 and 8), or with a combination of 1 nM $E_2$ and a 100-fold molar excess of ICI 182,780 (lanes 6 and 9). Positions of Flk-1, wild type ER, 42 kDa ER-reactive band and IL-8 are indicated.

DESCRIPTION OF THE PREFERRED EMBODIMENTS

Figure 1A:
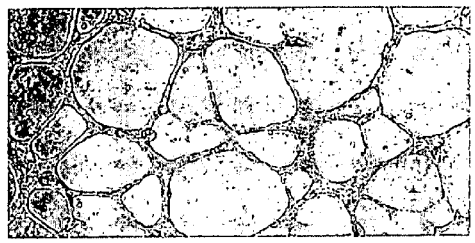
FIG. 1 shows phase contrast morphology of cells in 3D Matrigel culture. Panels a and b: MCF10A cells at 24 h and 10 days, respectively; Panels c and d: EIII8 cells at 24 h and 10 days, respectively; panels e and f: HUVEC cells at 24 h and 5 days, respectively. Note the difference in contrast on day 10 between MCF10A (b) and EIII8 (d) cultures that is produced by multilayering of epithelium. Bar 100 µm.
Figure 1B:
Figure 1C:
Figure 1D:
Figure 1E:
Figure 1F:
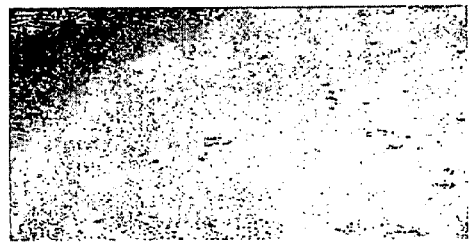
Figure 2A:
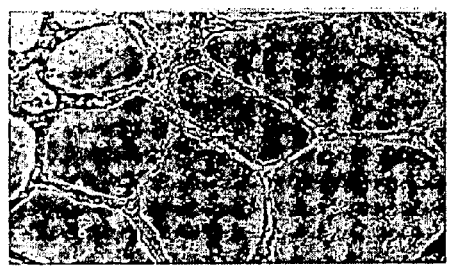
FIG. 2 shows phase contrast morphology of EIII8 cells in 3D Matrigel culture following treatment with estrogen. (Panel a) Cultures treated with 100 nM ICI 182,780; Panel b and d: cultures treated with 1 or 10 nM 17 β-estradiol ($E_2$), respectively; Panel c: cultures treated with a combination of 1 nM $E_2$ and a 100-fold molar excess of ICI 182,780. All cultures represent morphologies at 5 days of culture. Note the remarkable differences in contrast between cultures exposed to ICI 182,780 (panels a and c) and $E_2$ (panels b and d). Also, note that addition of ICI 182,780 significantly inhibits epithelial multilayering induced by $E_2$. Treatment with $E_2$ also induce formation of several new central spaces and connecting bridges (panels b and d). Bar 100 µm.
Figure 2B:
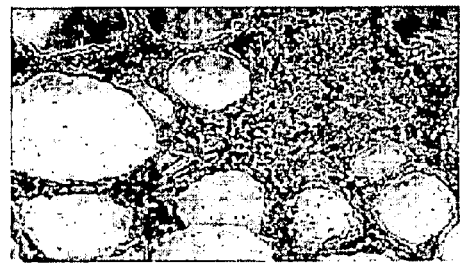
Figure 2C:
Figure 2D:
Figure 3A:
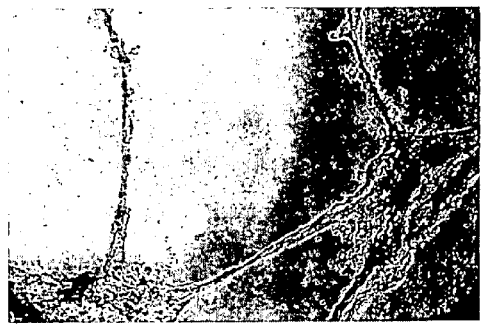
FIG. 3 shows phase contrast morphology of heterotypic EIII8-HUVEC or MCF10A-HUVEC co-cultures in Matrigel at day 5. MCF10A-HUVEC or EIII8-HUVEC cultures were treated with vehicle (0.01% ethanol, v/v; panels a and d, respectively), 1 nM $E_2$, (panels b and e, respectively), or a combination of 1 nM $E_2$ and a 100-fold molar excess of ICI 182,780 (c and f, respectively). Note the difference in the sizes of "endothelial cell enriched spots" (⇐) formed on EIII8- and MCF10A-epithelia. Also, note the specific association of "ductal-alveolar outgrowths" (arrows) with "endothelial cell enriched spots" in EIII8-HUVEC cultures (panels d and e), and the specific inhibition by ICI 182,780 of ductal-alveolar growth and endothelial cell enriched spots in EIII8-HUVEC (panel f) and endothelial cell growth in MCF10A-HUVEC cultures (panel c). The inset in panel f shows the results of exposure to ICI 182,780 for 14 days. Bar 100 µm.
Figure 3B:
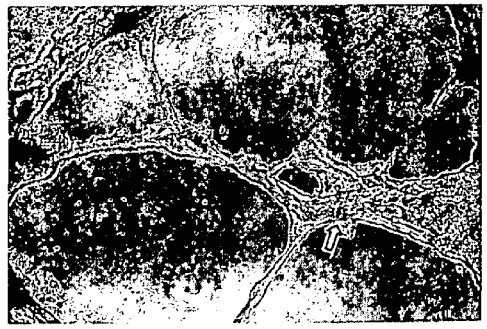
Figure 3C:
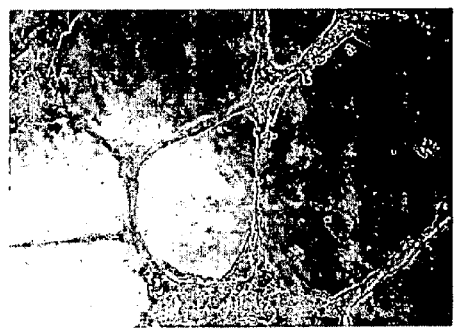
Figure 3D:
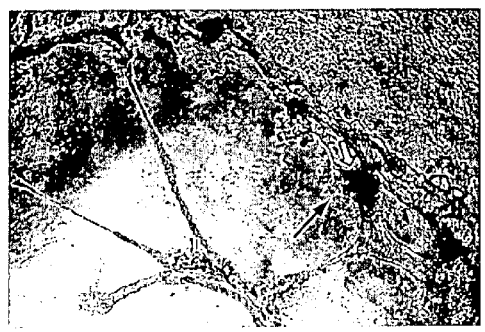
Figure 3E:
Figure 3F:
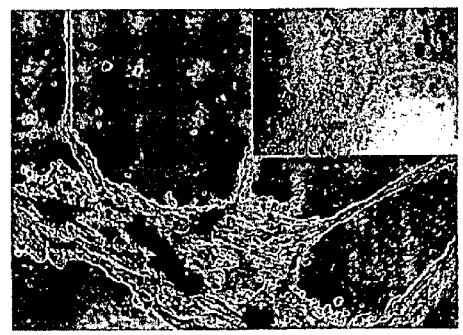
Figure 4A:
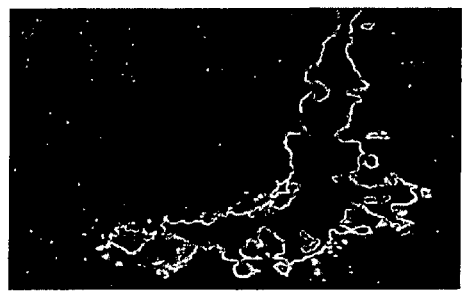
FIG. 4 shows phase contrast micrographs of 3D EIII8-HUVEC co-cultures. Panels a and b: co-cultures established with DiI- and DiO-prelabeled EIII8 and HUVEC cells, respectively. Note that ductal-alveolar outgrowths are comprised of epithelial cells (Panel a) whereas DiO-labeled endothelial cells are concentrated at this region as a spot (Panel b). Note the presence of immature buds at day 5 of culture (panels c and d) that have developed into distinct and well formed buds by day 10 (panels e and f). The dark areas in close association with alveolar structures represent the endothelial cell-enriched sites. Bar 100 µm (Panels a,b,c,e) and 50 µm (Panels d and f).
Figure 4B:
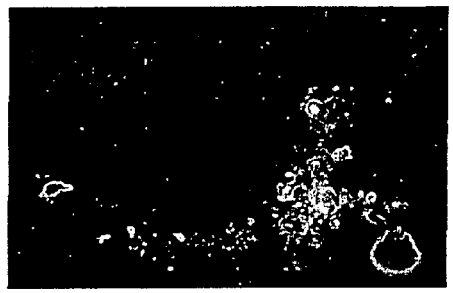
Figure 4C:
Figure 4D:
Figure 4E:
Figure 4F:

The present inventors have developed a three-dimensional (3D) in vitro culture system that supports growth and functional differentiation of preneoplastic human breast epithelial cells and endothelial cells, and recapitulates estrogen induced in vivo effects on angiogenesis and proliferative potential of MCF10AT xenografts. MCF10A and MCF10AT1-EIII8 ("EIII8") cell lines used in the development of this model are normal or produce preneoplastic lesions, respectively. When MCF10A or EIII8 cells are seeded on reconstituted basement membrane (e.g., Matrigel) both lines organize into a 3D tubular network of cells; however, tubes produced by EIII8 cells are multicellular in contrast to the unicellular structures formed by MCF10A cells.

However, when MCF10A or EIII8 cells are co-cultured with human umbilical vein endothelial cells (HUVEC) on Matrigel, rather than interacting with ECM, the endothelial cells exhibit preferential adherence to epithelial cells. Although both MCF10A and EIII8 cells provide preferential substrate for endothelial cell attachment, only EIII8 cells facilitate sustained proliferation of endothelial cells for prolonged periods resulting in visible" endothelial cell enriched spots" which express factor VIII-related antigen. At regions of endothelial enriched spots, preneoplastic human breast epithelial cells undergo branching ductal-alveolar morphogenesis, produce mucin, express cytokeratins and PCNA. The presence of actively proliferating and functional endothelial cells is essential for ductal-alveolar morphogenesis of preneoplastic human breast epithelial cells since without the endothelial cells, the epithelial cells form only tubular structures.

This ability to establish functional endothelial cells and ductal-alveolar morphogenesis is facilitated only by preneoplastic human breast epithelial cells—normal MCF10A cells fail to elicit similar effects. Thus, the present inventors have established a cause-effect relationship, that is mutually beneficial, between endothelial cells and preneoplastic human breast epithelial cells that is critical for generation of functional vascular networks and local proliferative ductal alveolar outgrowths with invasive potential.

Both these processes are augmented by estrogen and inhibited by antiestrogens. Induction and maintenance of angiogenic phenotype is associated with upregulation in expression of interleukin-8 (IL8) and matrix metalloproteinase-2 (MMP2). Estrogen-induces increases in VEGF and VEGF-receptor 2.

Using the 3D basement membrane assay system of this invention, the present inventors demonstrated a direct cause-effect relationship between endothelial cells and preneoplastic human breast epithelial cells which is integral for the generation of active angiogenesis and ductal-alveolar morphogenesis, two processes that are regulated by $E_2$ at the molecular and cellular levels. Furthermore, the abilities to undergo ductal-alveolar morphogenesis and establish an active angiogenic process depend on the cellular genotype of the human breast epithelial cells, since untransformed parental MCF10A human breast epithelial cells lack both these abilities. Finally, the present findings suggest that active angiogenesis is integral for growth and proliferative potential of "ductal-alveolar structures" which in turn may determine the malignant phenotype.

This 3D culture model offers a unique opportunity to study endothelial- and epithelial-cell specific factors that are important for ductal-alveolar morphogenesis, angiogenesis and progression to malignant phenotype.

Components of the Three-Cell Culture System

1. Breast or Mammary Epithelial Cells

These cells must be genetically altered from normal to yield the preneoplastic morphology described herein, though not enough to be oncogenically transformed. For example, MCF-7 and MDA series cells are tumorigenic with non-metastatic and metastatic properties, respectively, in vivo but do not produce the characteristic morphology of the culture system of the present invention.

Preferred mammary epithelial cell lines are described in the Examples below. Epithelial cells may be evaluated for their utility in the present culture system based upon their behavior in vivo upon implantation into immunocompromised, e.g., nude, mice. When implanted subcutaneously or into mammary fat pads of such mice along with an ECM such as Matrigel, these cells recapitulate the early stages of human preneoplastic breast disease resulting in histological pictures ranging from mild hyperplasia to ductal carcinoma in situ.

Preneoplastic cells may be obtained directly from a subject with breast disease and placed in culture, optionally followed by serial subculture or even establishment of a cell line. Methods of preparing tissues, growing the cells including under cloning conditions, as well as useful culture media for mammary epithelial cells, are disclosed in U.S. Pat. No. 4,423,145, which is hereby incorporated by reference in its entirety.

2. Endothelial Cells

Any source of endothelial cells may be used, and these cells may be from a different species of origin that the breast epithelial cells or fibroblasts. A preferred source is HUVEC.

3. Breast Fibroblasts

These cells must be breast fibroblasts from the same species as the breast epithelial cells, preferably human. The interaction of the breast epithelial cells with this stromal element are important in the development of the ductal morphology of this culture system.

Growth and Culture Conditions

Each cell type that constitutes the 3D cultures of the present invention is maintained separately under conditions that are optimal for each of the three particular types of cells.

Breast epithelial cells do not have stringent growth requirements. As described in the Examples, these cells grow best in medium such as DMEM-F12 that is supplemented with 0.1 $\mu$g/ml cholera toxin, 10 $\mu$g/ml insulin, 0.5 $\mu$g/ml hydrocortisone, 0.02 $\mu$g/ml epidermal growth factor (EGF), 100 i.u./ml penicillin, 100 $\mu$g/ml streptomycin and 2.5% horse serum. The sera should be pretested for the lack of biologically significant levels of estradiol ($E_2$) or other estrogenic compounds.

The co-culture system of this invention should include the epithelial cell growth promoting substances cholera toxin, insulin, hydrocortisone and EGF, though the concentrations may be reduced to as little as $\frac{1}{10}$ the above concentrations because some of the growth stimuli will be provided by the co-culture cell partners.

For endothelial cell culture, bFGF, FGF and fibronectin are required. These cells are preferably maintained in a medium such as the commercially available Endothelial Serum Free Basal growth Medium ("SFM") from Gibco BRL. The medium is supplemented, in accordance with the supplier's instructions, with EGF (10 ng/ml), bFGF (20 ng/ml) and fibronectin (10 $\mu$g/ml). Cultures are maintained at 37° C. in a humidified atmosphere containing 5% $CO_2$ in air.

As above, in the context of the culture system of this invention involving co-culture of breast epithelial cells, endothelial cells and fibroblasts, the above concentrations may be lowered to as low as $\frac{1}{10}$ that indicated above because the additional cell types provide growth stimuli or factors.

Estrogens

The culture system of the present invention is preferably supplemented with an estrogen such as E2 at concentrations between about 1 and 10 nM. Early changes occurring in the preneoplastic breast epithelial cells are due to the presence of estrogen receptors (ER's) in these cells. In the present culture system, the more rapid development in the particular morphology representing preneoplastic breast disease is promoted by the presence of estrogen in the medium, as it can act on ER's of both breast epithelial cells and endothelial cells. In endothelial cells, estrogens promote massive angiogenesis. Although angiogenesis per se is not part of the present in vitro system, the tube formation that is considered to be related to angiogenic activity is believed to contribute the morphological developments of these 3D cultures.

There is no requirement for serum in the present culture system, as the important components are provided as supplements, as indicated above. However, that is not to say the a serum source may not be used in the present system. For example any conventional serum source, such as human AB serum, fetal bovine serum, horse serum, may be used at concentrations between about 0.1 and 10% v/v. There is no requirement that the serum be from the same species as the cells.

Evaluation of Culture Morphology

Morphology or the culture system is described in more detail in the Examples, and Figures are presented herein that show the various changes that occur. Primarily, the present culture system is designed to yield morphological changes consistent with preneoplastic breast disease. The hallmark feature is the development of branching ductal alveolar units. Other changes characteristic of preneoplastic breast disease include anything from simple/mild hyperplasia (grades 0/1) to atypical hyperplasia (grade 3) and ductal carcinoma in situ (grade 4) (see Table 1).

Morphological analysis and morphometry can be performed using standard histological techniques as well as image analysis. Counts of branches in a given region can be carried out on whole mounts of individual cultures.

Direct Assay of Cell Proliferation in Culture System

This is done essentially as described in the Examples, below. Cells in the present culture system are incubated at 37° C. for about 5 days, after which cell viability is measured with the MTS (3-(4,5-dimethylthiazol-2-yl)-5-(3-carboxymethoxyphenyl)-2-(4-sulfophenyl)-2H-tetrazolium), for example, using a kit sold by Promega Corp). Measurements are preferably from triplicate wells for each treatment. Background absorbance is corrected by preparing triplicate sets of wells containing only Matrigel ("no cell") and the same volume of medium and MTS reagent as in experimental wells. Average absorbances from "no cell" wells are subtracted from sample absorbance values containing cells to yield corrected absorbance Each experiment is preferably repeated at least three times. Since the MTS assays performed here differs from routine MTS assays in that they are done on 3D cultures growing in Matrigel rather than monolayers, results of MTS assays can be validated by performing direct cell counts of viable cells in the 3D cultures. For this, the medium is removed. (This medium may assayed for growth or angiogenic factors as described herein, either immediately or after frozen storage, as described herein). The wells are rinsed with PBS, and Matrigel is digested with dispase. The digested material is centrifuged and the pellet treated with trypsin to recover single cells from the 3D tubular structures. The number of viable cells are determined by trypan blue exclusion in a hemocytometer.

Assay of Culture Supernatants for Various Activities

Immunoassay

The presence or quantity of any given factor, e.g., VEGF, in the culture supernatant can be assayed using a specific antibody, preferably a monoclonal antibody, in any standard immunoassay. Preferred assays are solid phase Enzyme Immunoassays (EIA) or ELISA. Such assays are described in greater detail in: Butler, J E, *The Behavior of Antigens and Antibodies Immobilized on a Solid Phase* (Chapter 11) In: *STRUCTURE OF ANTIGENS*, Vol. 1 (Van Regenmortel, M, CRC Press, Boca Raton 1992, pp. 209–259; Butler, J E, ELISA (Chapter 29), In: van Oss, C. J. et al. (eds), *IMMUNOCHEMISTRY*, Marcel Dekker, Inc., New York, 1994, pp. 759–803 Butler, J E (ed.), *IMMUNOCHEMISTRY OF SOLID-PHASE IMMUNOASSAY*, CRC Press, Boca Raton, 1991; Butler, J E, *Meth. Enzymol.* 73:482–523 (1981); Maggio, E. (ed.), *ENZYME IMMUNOASSAY*, CRC Press, Boca Raton, 1980.

Protease Activity

The matrix metalloproteinase (MMP) family of proteases (Moses, M. A. et al., Science 248:1408–1410, 1990; Mignatti, P et al., J. Cell Biol., 108:671–682, 1988; Johnson, M. D. et al., J. Cell Physiol.,160:194–202, 1994) are released by cells of the present culture system when they are stimulated to grow and develop the disclosed morphology. One way to assay the supernatant for these enzyme activities is by testing the gelatinolytic activity, by gelatin zymography, of the conditioned medium (see Examples). Both latent or pro-forms of enzymes and active forms of the enzyme may be present, though significantly elevated levels of the active form are found in the conditioned medium of the active cultures (e.g., EIII8-HUVEC co-cultures. Controls are included to rule out the presence of contaminating enzyme that is secreted from Matrigel during culture (Schnaper, H. W. et al, J. Cell Physiol., 166:235–246, 1993). In general, the protease activity of these enzymes can be assayed in any of a number of conventional assays.

Cell Proliferation

The proliferation-inducing activity of the culture supernatant obtained from the present culture system may be determined using various cell types, particularly endothelial cells and fibroblasts.

1. Incorporation of Radiolabel

A typical assay would involve plating cells at a density of 5–10,000 cells per well in a 96-well plate. The supernatant to be tested is added at various dilutions and allowed to incubate with the cells for 4 days. The cells are washed several times with medium, then fresh medium containing [$^3$H]thymidine (1 $\mu$Ci/mL) is added to the cells and they are allowed to incubate at 37° C. in 5% $CO_2$ for 24 hours. Cells are lysed at the various time points using 1 M NaOH and counts per well determined in a liquid scintillation counter.

2. Colorimetric Assay

Proliferation may be measured non-radioactively using MTS reagent (see Examples, below) or CyQuant® to measure total cell number before and after treatment, or at various times of culture.

Biological Assay of Angiogenic Activity

The culture medium from the present culture system is tested for angiogenic activity in one of two different assay systems in vitro. endothelial cells, for example, HUVEC or human microvascular endothelial cells (HMVEC) which can be prepared or obtained commercially, are mixed at a concentration of $2 \times 10^5$ cells/mL with fibrinogen (5 mg/mL in phosphate buffered saline (PBS) in a 1:1 (v/v) ratio. Thrombin is added (5 units/mL final concentration) and the mixture is immediately transferred to a 24-well plate (0.5 mL per well). The fibrin gel is allowed to form and then the test medium is added to the wells (at various dilutions. The cells are incubated at 37° C. in 5% $CO_2$ for 4 days at which time the cells in each well are counted and classified as either rounded, elongated with no branches, elongated with one branch, or elongated with 2 or more branches. Results are expressed as the average of 5 different wells for each concentration of compound. Typically, in the presence of angiogenic agents, cells form branched tubes (>1 branch).

This assay is recognized in the art to be predictive of angiogenic efficacy in vivo (Min, H Y et al., Cancer Res. 56:2428–2433, 1996.

In an alternate assay, endothelial cell tube formation is observed when endothelial cells are cultured on Matrigel® (Schnaper, H W et al., J. Cell. Physiol. 165:107–118, 1995). endothelial cells ($1 \times 10^4$ cells/well) are transferred onto Matrigel®-coated 24-well plates, and tube formation is quantitated after 48 hrs. This assay models angiogenesis by presenting to the endothelial cells a particular type of basement membrane, namely the layer of matrix which migrating and differentiating endothelial cells might be expected to first encounter. In addition to bound growth factors, the matrix components found in Matrigel® (and in basement membranes in situ) or proteolytic products thereof may also be stimulatory for tube formation which makes this model complementary to the fibrin gel angiogenesis model previously described (Blood, C et al., Biochim. Biophys. Acta 1032: 89–118, 1990; Odedra, R et al., Pharmac. Ther. 49: 111–124, 1991).

In summary, this culture system has a number of applications:

(1) Research utility: The culture system is used to explore the mechanisms involved in preneoplastic breast disease and the progression to breast cancer, processes that inhibit or block this course, the role of angiogenesis in the process and the role of fibroblast-epithelial interactions.
(2) Drug screening utility: The culture system is used to evaluate mechanisms and actions of new or existing drugs, biologicals or therapeutic regimens that are used in chemoprevention and/or treatment of preneoplastic breast disease and breast cancer. This model has major applicability not only in screening and evaluating new agents but also in re-establishing and re-evaluating known drugs, e.g.,
   (a) drugs that selectively inhibit angiogenesis and thus block, neoplastic conversion;
   (b) drugs that directly inhibit alveolar morphogenesis by acting on epithelial cells;
   (c) drugs that induce terminal differentiation thereby inhibiting neoplastic conversion;
   (d) drugs that inhibit proteolytic enzymes which are key to invasion and to transformation to malignancy.

Progression to Neoplastic Disease

One clearly observable morphological change in neoplastic progression in the present cultures is a hyperproliferative phase. In co-cultures of two cells types (epithelial-fibroblast or epithelial-endothelial), several buds are seen to form. However, in the three cell cultures of the present invention, not only is an increase in the density of alveolar outgrowths observed, but expansions resembling a "mass" occur, possibly resulting from failure to differentiate into buds. The presence of carcinoma can also be shown by histological analysis.

Thus, to determine if an agent promotes or inhibits neoplastic progression, using the present model, histological analysis of the cultures is performed as described herein, including hematoxylin/eosin staining. In addition, the cultures are examined for the presence of, or changes in, distribution and localization of specific differentiation markers for angiogenesis and epithelial cells, and/or loss of differentiation markers or gain in expression of genes that are related to acquisition of invasive potential. Relevant markers that are examined or measured include:

(1) proteases
(2) altered cell cycle regulatory markers, such as cyclins (especially cyclin D, p53, Rb, bcl-2, bax, p21, c-fos and c-jun (AP-1).
(3) signal transduction markers such as EGF receptor, erbB-2, TGF-β receptors, ras, MAP kinase, MAP kinase kinase (and the like).
(4) nuclear receptors such as estrogen receptor, co-activators (e.g., SRC-1) and co-repressors (NCoR1), retinoic acid receptors.

For a discussion of such markers and methods for detecting or measuring them, see, for example, Dickson R B et al., *Molecular Basis of Breast Cancer*, In: THE MOLECULAR BASIS OF CANCER (Mendelsohn J et al., eds., Saunders Co., Philadelphia (1995), pp358–384; Mendelsohn, J. et al., *Growth factors in malignancy* (supra at pp. 432–459); Murakami M S et al., *Cell cycle regulation, oncogenes and antineoplastic drugs*, supra at pp. 3–17). The entire volume is hereby incorporated by reference.

Having now generally described the invention, the same will be more readily understood through reference to the following examples which are provided by way of illustration, and are not intended to be limiting of the present invention, unless specified.

EXAMPLE I

Materials and Methods

Cell Lines

The MCF10AT system is a xenograft model of progressive human proliferative breast disease in which the progression of a T24-Ha-ras transformed derivative of MCF10A (Soule, H. D. et al., Cancer Res., 50: 6087–6094, 1990) designated MCF10AneoT (Basolo, F. et al., *Mol. Carcinogen.* 4:25–35, 1991) can be followed in immunodeficient mice from a histologically precancerous stage to development of frank invasive carcinoma (Miller, F. R. et al., *J. Nat. Cancer Inst.*, 85:1725–1732, 1993).

MCF10A cells do not form persistent lesions in immunodeficient mice, whereas MCF10AneoT cells do (Miller et al., supra). MCF10AneoT and lines derived by alternating in vivo transplantation and in vitro culture (MCF10ATn) are collectively known as the MCF10AT system (Dawson, P. J. et al., Am. J. Pathol., 148:313–319, 1996). The lesions formed by lines of the MCF10AT system are composed of a heterogeneous spectrum of ductal tissues with a range of morphologies: mild to moderate hyperplasia, atypical hyperplasia, carcinoma in situ (CIS), moderately differentiated carcinoma, and undifferentiated carcinoma, as well as histologically normal ducts (Miller et al, supra). This system provides a transplantable, xenograft model of human proliferative breast disease with proven neoplastic potential.

These studies utilized parental MCF10A cells and the following lines of the MCF10AT xenograft model: MCF10AT1 and MCF10AT1-EIII8 ("EIII8"). MCF10AT1 represents the first transplant generation of the MCF10AT xenograft model. EIII8 cells are breast preneoplastic epithelial cells that were derived from lesions of MCF10AT1 cells arising in $E_2$-supplemented animals (Shekhar et al., supra) and respond to $E_2$ with increased growth in vitro and in vivo. MCF10A and MCF10AT-derived cells were maintained in phenol red-free DMEM-F12 medium supplemented with 0.1 µg/ml cholera toxin, 10 µg/ml insulin, 0.5 µg/ml hydrocortisone, 0.02 µg/ml epidermal growth factor (EGF), 100 i.u./ml penicillin, 100 µg/ml streptomycin and 2.5% horse serum. Charcoal-stripped serum was not used as it reduced both the viability and proliferative capacity of MCF10A cells. The only sera used routinely were those which were unable to support growth of the estrogen-dependent cell line, MCF-7, indicating absence of biologically significant levels of $E_2$ or other estrogenic compounds.

HUVECs purchased from American Type Culture Collection at passage 13 were maintained in Endothelial Serum Free Basal growth Medium ("SFM"; Gibco BRL Life Technologies, Grand Island, N.Y.) supplemented with EGF (10 ng/ml), basic fibroblast growth factor (bFGF; 20 ng/ml) and fibronectin (10 µg/ml). Cultures were maintained at 37° C. in a humidified atmosphere containing 5% $CO_2$ in air.

Primary cultures of human breast fibroblasts were established from tissue obtained during mammoplasty ("normal"), from tumors and from benign tissues ipsilateral, but distal, to the tumors acquired after protocol review and approval by the Wayne State University human investigation committee (Pauley, R. J. et al., J. Clin. Endocrinol. Metabol., 85: 837–846, 2000). Tumors confirmed by histology, were finely minced and digested overnight with collagenase (150 IU/ml) in DMEM/Ham's F-12 (1:1) containing 20% calf serum. Larger pieces were allowed to settle, and cells in the supernatant, predominantly fibroblasts, were recovered by centrifugation and plated in Weymouth's MB752 supplemented with 10 mmol/L HEPES and 15% fetal calf serum (FIB; Pauley et al., supra). Reduction mammoplasty and benign tissues were digested as above with addition of hyaluronidase (100 IU/ml), and further processed as described for tumors. Portions of normal and benign tissues used for culture were examined histologically to confirm the absence of neoplasia. Fibroblasts were routinely cultured up to 15 passages and were used at passages 4 to 6. Fibroblasts were characterized immunocytochemically with monoclonal antibodies to pan cytokeratin (Dako Corp., Carpentaria, Calif.), cytokeratin 14 (Novacastra, Newcastle upon Tyne, UK), and vimentin (V9; Dako Corp.) as described in Pauley et al., supra). Normal human lung fibroblasts (IMR-90) and the mesenchyme derived malignant human fibrosarcoma cell line HT1080 were obtained from ATCC and maintained in Eagle's Minimum essential medium supplemented with 2 mM L-glutamine, 0.1 mM non-essential amino acids, 1.0 mM sodium pyruvate, and 10% fetal bovine serum. The NIH 3T3 mouse embryo fibroblast line was purchased from ATCC and maintained in Dulbecco's modified Eagle's medium supplemented with 4 mM glutamine, 4.5 g/L glucose, 1.0 mM sodium pyruvate, and 10% fetal calf serum.

Homotypic and Heterotypic 3-Dimensional Basement Membrane Culture of MCF10A, EIII8 and HUVEC Cells For homotypic 3D cultures, $10^5$ cells were seeded as a single cell suspension in 8-well chamber slides coated with Matrigel (Collaborative Biomedical Products, Bedford, Mass.), in DMEM-F12-supplemented media for MCF10A cells and its derivatives, in SFM-supplemented media for HUVECs, in FIB medium for human breast fibroblasts, or in the appropriate medium for IMR-90, HT1080 or NIH 3T3 cells as described above.

For heterotypic 3D co-cultures, $5 \times 10^4$ MCF10A, MCF10AT1, or EIII8 cells were mixed with an equal number of HUVECs, human breast fibroblasts (reduction mammoplasty, benign or tumor-derived), IMR-90, HT1080 or NIH 3T3 cells.

For heterotypic tricultures, MCF10A or EIII8 cells were mixed with equivalent numbers of human breast fibroblasts (reduction mammoplasty, benign or tumor-derived) and HUVECs and seeded onto chamber slides coated with Matrigel as described for homotypic cultures. Typically, heterotypic co-cultures were performed in SFM supplemented with EGF and bFGF since this medium results in optimal viability, growth and 3D organization of both HUVEC and MCF10A cells.

Typically, heterotypic cultures were performed in SFM supplemented with EGF and bFGF because it allows optimal viability, growth and 3D organization of HUVEC, fibroblasts and MCF10A cells. Heterotypic co-cultures were routinely maintained up to 3 weeks, and morphological development was analyzed by phase contrast microscopy. F The interaction between EIII8 and HUVEC cells was determined by prelabeling them with the fluorescent cationic membrane tracers, 1,1'-dioctadecyl-3,3,3',3'-tetramethylindocarbocyanine perchlorate (DiI) and 3,3'-dilinoleyloxacarbocyanine perchlorate (DiO; Molecular Probes, Inc., Eugene, Oreg.), respectively, prior to co-culturing. These brightly fluorescent dyes diffuse laterally within the plasma membrane resulting in uniform staining of the entire cell, and since transfer of these probes between intact membranes is negligible and cytotoxic effects are minimal, they permit long-term cell tracking in the 3D-cultures.

Quantitation of Effects of Interaction of Preneoplastic Breast Epithelial Cells with Reduction Mammoplasty/Tumor-Derived Breast Fibroblasts and EC's on 3-Dimensional Growth.

3-D cultures were set up by seeding $5 \times 10^4$ EIII8, HUVEC, 31R or 14R (reduction mammoplasty fibroblasts), 38T or 12T (tumor-derived breast fibroblasts) alone or mixing $5 \times 10^4$ EIII8 cells with an equivalent number of 31R (or 14R) or 38T (or 12T) in the absence or presence of an equivalent number of HUVEC cells onto chamber slides coated with Matrigel as described above. Cultures were incubated at 37° C. for 6 days, after which the cell viability was measured in the 3-D cultures. The medium was removed, wells were rinsed with phosphate buffered saline, and the Matrigel was digested with dispase for 2 h at 37° C. The digested material was centrifuged at 4000×g for 10 min, and the pellet was treated with trypsin to recover single cells from the 3-D structures. The number of viable cells was determined by trypan blue exclusion in a hemocytometer and results expressed as average±SE from three independent experiments.

The effects of $E_2$ and the pure antiestrogen ICI 182,780 (a gift from Dr. A. Wakeling, Zeneca Pharmaceuticals, Cheshire, United Kingdom) on 3-D growth of heterotypic cultures of EIII8/31R/HUVEC and EIII8/38T/HUVEC cells were tested as described above except that after seeding of cells, slides were incubated overnight to allow cells to attach to the surface and treated with vehicle (0.01% ethanol, v/v), 100 nM ICI 182,780, 1 or 10 nM 17 β-estradiol ($E_2$, Sigma Chemical Co., St. Louis, Mo.) or a combination of 1 nM $E_2$ and 100-fold molar excess of ICI 182,780. In some experiments, different concentrations of these agents were used (as indicated).

Preparation of Conditioned Media $5 \times 10^4$ EIII8 or MCF10A cells were seeded alone or mixed with an equivalent number of HUVEC on Matrigel in SFM media as described above. Cells were incubated for 6 h to attach and the medium was replaced with fresh SFM. After appropriate incubation, the culture media from homotypic and heterotypic co-cultures were collected, centrifuged to remove debris and stored at −20° C. Following removal of culture medium, matrix containing the 3D structures was either solubilized for SDS-PAGE and Western blot analysis or fixed in buffered formalin for evaluation of morphology and distribution of functional markers.

Effect of Conditioned Medium on Proliferation of HUVEC Cells $10^4$ HUVEC were plated in SFM supplemented with EGF, fibronectin and bFGF in 24 well plates. Eight h later, various volumes of unconcentrated conditioned medium prepared from homotypic EIII8 or MCF10A cultures, or heterotypic MCF10A-HUVEC or EIII8-HUVEC co-cultures, were added. For inhibition experiments, several antibodies were used: (1) polyclonal antibodies to human VEGF (specific for a C-terminal epitope found in $VEGF_{165}$, $VEGF_{189}$ and $VEGF_{206}$; Oncogene Science, Cambridge, Mass.), (2) mouse monoclonal antibody (mAb) to human Flk1/KDR (epitope not known; Chemicon International, Inc., Tamecula, Calif.) and (3) polyclonal antibody to human IL-8 (<5% cross-reactivity with Groα, Groβ, and Groγ; R&D Systems, Minneapolis, Minn.). The antibody preparation was diluted in SFM and added to cultures at 10 µg/ml. Appropriate non-immune control IgG was used at 10 µg/ml. Cultures were incubated at 37° C. in 5% $CO_2$-95% $O_2$ for 5 days with medium change and supplementation of conditioned medium or appropriate antibodies every other day. Cells were released by trypsinization and viable cells, as demonstrated by trypan blue exclusion, were counted in a hemocytometer. All cell counts were done from triplicate wells and results were expressed as the mean±standard error (S.E.) from three independent experiments.

Western Blot Analysis

Analysis of expression of VEGF, IL-8, Estrogen receptor (ER) and Flk-1/KDR proteins was carried out by Western analysis with specific antibodies. Aliquots of unconcentrated conditioned media or lysates of 3D cultures containing 20 or 40 µg total protein, respectively, were collected after indicated culture intervals, separated by SDS-PAGE on 12.5% (VEGF), 17% (IL-8) or 7% (ER and Flk-1/KDR) polyacrylamide gels (Laemmli, UK, Nature 227:680–685, 1970), and subjected to Western blot analysis. The following antibodies to human proteins were used: (1) rabbit polyclonal anti-VEGF antisera (recognizes C-terminal epitope of $VEGF_{165}$, $VEGF_{189}$ and $VEGF_{206}$; Oncogene Science), mouse anti-ER mAb (Clone 1D5; reacts with the N-terminal domain or A/B region of the ER; Dako Corp., Carpenteria, Calif.), mouse anti-Flk-1/KDR mAb (Chemicon International, Inc.) and goat polyclonal anti-IL-8 antibody (R&D Systems). Immunoreactive bands were visualized by chemiluminescence, and band intensities were quantitated with a Model 300A densitometer (Molecular Dynamics, Sunnyvale, Calif.).

Evaluating Effects of Estrogen on 3D Culture Growth

To assess growth effects of $E_2$ on homotypic (EIII8) or heterotypic (EIII8-HUVEC) 3D cultures, $5 \times 10^4$ EIII8 cells were seeded alone or mixed with an equivalent number of HUVEC in the appropriate medium in 8-well chamber slides coated with Matrigel as described above. Slides were incubated overnight to allow attachment of the cells, and treated with vehicle (0.01% ethanol, v/v), pure antiestrogen ICI 182,780 alone (100 or 1000 nM (Zeneca Pharmaceuticals, Cheshire, U.K.), $E_2$ (0.1, 1 or 10 nM; Sigma Chemical Co., St. Louis, Mo.), or a combination of 1 nM $E_2$ and 100- or 1000-fold molar excess of ICI 182,780. Cultures were incubated at 37° C. for 5 days, after which cell viability was measured with the MTS (3-(4,5-dimethylthiazol-2-yl)-5-(3-carboxymethoxyphenyl)-2-(4-sulfophenyl)-2H-tetrazolium) kit according to the manufacturer's directions (Promega Corp, Madison, Wis.).

Measurements were made from triplicate sets of wells for each treatment. Background absorbance was corrected by preparing triplicate sets of wells containing only Matrigel ("no cell") and the same volume of medium and MTS reagent as in experimental wells. Average absorbances from "no cell" wells were subtracted from sample absorbance values containing cells to yield corrected absorbance, and the results represent the average±S.E. of triplicate samples. Each experiment was repeated at least three times. Since the MTS assays performed here differs from routine MTS assays in that they are done on 3D cultures growing in Matrigel rather than monolayers, results of MTS assays were validated by performing direct cell counts of viable cells in the 3D cultures. For this, the medium was removed, wells rinsed with PBS, and Matrigel was digested with dispase for 2 h at 37° C. The digested material was centrifuged at 4000×g for 10 min, and the pellet treated with trypsin to recover single cells from the 3D tubular structures. The number of viable cells was determined by trypan blue exclusion in a hemocytometer. Results were expressed as mean±S.E. from three independent experiments.

Morphological Evaluation

Whole mounts of EIII8-12T co-cultures were prepared by staining formalin-fixed cultures with toluidine blue and mounted on slides with Permount (Russo, J. et al., Breast Cancer Res. Treatment, 23: 211–218, 1992).

For histological evaluation, 3D co-cultures (such as EIII8-12T or EIII8-12T-HUVEC) were fixed in buffered formalin, embedded in paraffin, and 4 µm sections stained with hematoxylin and eosin (H&E).

For immunohistochemical evaluation of breast epithelial, fibroblast and endothelial cell functional markers, sections were incubated with mAbs specific for the following human proteins: pan-cytokeratin 5/6/8/18 is a cocktail of mAbs designed to recognize epithelial cells and their tumors (Novocastra Laboratories Ltd., Newcastle-upon-Tyne, UK); vimentin (V9; Dako Corp.); muc-1 glycoprotein, a mammary type apomucin also known as milk fat globule membrane antigen (Novocastra Laboratories Ltd.); cd31 or PECAM-1 (Dako Corp.); Factor VIII related antigen (Dako Corp.); Ki-67 (Dako Corp.); VEGF receptor-2 (Chemicon International, Inc., Tamecula, Calif.); $\alpha_v\beta_3$ integrin (Chemicon International, Inc.), MMP-9 (Oncogene Science, Cambridge, Mass.); rabbit polyclonal antibody to VEGF (Oncogene Science); and rabbit polyclonal antibody against proliferating cellular nuclear antigen (PCNA; Dako Corp.). In each instance, negative controls were overlaid with appropriate mouse or rabbit IgG isotype. The slides were overlaid with avidin-biotin conjugated goat anti-mouse or goat anti-rabbit IgG (Vectastain ABC kit; Vector Laboratories, Burlingame, Calif.), incubated in peroxidase substrate solution (3,3'-diaminobenzidine), and counterstained by Mayer's hematoxylin (Sigma Chemical Co.).

Gelatin Zymography

The activity of gelatinolytic enzymes in conditioned media of MCF10A, EIII8, HUVEC, MCF10A-HUVEC or EIII8-HUVEC 3D cultures was detected by PAGE in 7.5% (w/v) gels containing gelatin at a final concentration of 0.6 mg/ml. Aliquots of conditioned medium containing equivalent amounts of protein were mixed with SDS-sample buffer (Laemmli, supra) and electrophoresed under nonreducing conditions. Following electrophoresis, the gel was soaked for 10 min in 2.5% Triton X-100/10 mM Tris-HCl, pH 8.0 at room temperature, rinsed and incubated at 37° C. for 16 h in 5 mM $CaCl_2$/50 mM Tris-HCl, pH 8.0. Gels were stained with 0.1% Coomassie Brilliant Blue R250 and destained. Purified precursor form of MMP-2 (pro-MMP-2; from Dr. Rafael Fridman, Wayne State University, Detroit, Mich.) was activated with 1 mM 4-aminophenylmercuric acetate (APMA) and used as a positive control for the activated MMP-2 form (Ishibashi, M. et al., Biochem J 241:527–534, 1987).

Statistical Analysis.

Data were analyzed by analysis of variance. Specific differences among treatments were examined using Student's t-test, where $p<0.02$ was considered as statistically significant.

EXAMPLE II

Three-Dimensional Basement Membrane Co-Culture of EIII8 Cells with HUVEC Recapitulate the Phenotypic Characteristics of Preneoplastic Breast Tissue In Vivo (see also Shekhar, P.V.M. et al., Cancer Res., 60: 439–449, 2000, which is incorporated by reference in its entirety)

1. Effects of Estrogen on 3D Growth of Homotypic Cultures

When MCF10A cells or ras-transformed MCF10AT1 or EIII8 cells were seeded on Matrigel, within 24 h all the lines organized into a 3D tubular network of cells that were arranged in a duct-like pattern around a central space (FIG. 1, panels a–d). Profound differences between the duct-like structures of EIII8 cells and MCF10A cells became evident after about 4 days in culture. Tubes produced by EIII8 cells appeared multicellular in contrast to the unicellular structures formed by MCF10A cells. The lack of tubular thickening was not due to loss of viability of MCF10A cells as these tubular structures were stable and persisted indefinitely as did those formed by EIII8 cells. Rather, this difference was due to difference in proliferative capacities of EIII8 and MCF10A cells on Matrigel (FIG. 1, compare panels a and b with c and d) although the two cell lines have similar doubling times (~19 h) on tissue culture plastic.

Since MCF10AT1 cells exhibited growth characteristics intermediate to those of MCF10A and EIII8 cells, the present studies concentrated on EIII8 cells. A major difference between MCF10A and EIII8 cells was the growth stimulatory effects of $E_2$ on EIII8 3D structures. Treatment with 1 or 10 nM $E_2$ resulted not only in marked thickening of tubes over those of control cultures but also in the formation of several new "central spaces" and "connecting bridges" (FIG. 2, compare panels b & d with panel a). These effects could be blocked by a 100-fold molar excess of the pure antiestrogen, ICI 182,780, indicating the specificity of $E_2$-induced effects (FIG. 2, panel c).

In contrast to stable tubular networks formed by the breast epithelial cell lines, similar cultures of HUVEC in Matrigel resulted in formation of tubes within 24 h that remained stable only for about 48–72 h, disintegrating by day 5 of culture (FIG. 1, panels e & f).

2. Heterotypic Cultures and Effects of $E_2$ on Growth

The inventors compared the abilities of normal MCF10A and preneoplastic EIII8 cells to support and maintain endothelial cell growth. When heterotypic co-cultures of MCF10A or EIII8 cells with HUVEC cells were established, the tubular networks observed with the homotypic cultures (FIGS. 1 and 2) were preserved. However, although equal numbers of epithelial and endothelial cells were seeded, the tubular frameworks were comprised mainly of epithelial cells while endothelial cells preferentially attached and proliferate at certain sites of the tubular framework. These regions, referred to as "endothelial cell-enriched spots," became prominent at about 2–3 days of culture (FIG. 3, panels a, b, d and e).

This distribution pattern of the two cell types in the 3D structures was confirmed in co-cultures of EIII8 and HUVEC hat were prelabeled with DiI and DiO, respectively (FIG. 4, panels a and b). It is interesting to note that while both MCF10A and EIII8 cells provided "soil" for endothelial cell attachment, only EIII8 cells sustained active proliferation of endothelial cells for >3 weeks. This was evident from the remarkable difference in sizes and capillary outgrowths of endothelial cell-enriched spots formed between EIII8-HUVEC and MCF10A-HUVEC co-cultures (FIG. 3; compare panels a, b and d, e). The endothelial cell-enriched spots present on MCF10A-induced tubular networks remained viable for only about one week although the epithelial framework persisted.

These results suggested major differences in the angiotropic response between normal and transformed human breast epithelial cells, i.e., whereas MCF10A cells switched from a pro-angiogenic to an anti-angiogenic phenotype, preneoplastic EIII8 cells remain turned-on in the pro-angiogenic state.

Another interesting feature unique to EIII8-HUVEC 3D cultures, and not observed in MCF10A-HUVEC co-cultures, was the development within 2–3 days of branching end buds or ductular-alveolar outgrowths in close proximity with endothelial cell-enriched spots (FIG. 3, panels d and e; FIG. 4, panels a–f). Treatment with 1 nM $E_2$ enhanced both growth of endothelial cell-enriched spots and ductal-alveolar outgrowths over those of control cultures as seen by an increase in size of both spots and ductal branches in 5-day co-cultures (FIG. 3, compare panels d and e).

Although no sera and only phenol red-free media were used, the magnitude and specificity of $E_2$-mediated stimulatory effects on angiotropic response and ductal-alveolar morphogenesis/growth became more obvious when cultures were treated with a combination of 1 nM $E_2$ and a 100-fold molar excess of 4(OH) tamoxifen or the pure antiestrogen ICI 182,780. By day 5, these cultures showed dramatic inhibition of both endothelial sprouting and associated ductal-alveolar morphogenesis (FIG. 3 panel f) that disintegrated by day 10–14 (FIG. 3 panel f, inset). These results suggested that the presence of contaminating estrogen in the culture media probably contributed to endothelial cell growth and ductal-alveolar morphogenesis observed in control cultures (FIG. 3, panel d). Although addition of $E_2$ to MCF10A-HUVEC co-cultures had no significant influence on growth and proliferation of endothelial cells or epithelial cells (FIG. 3, panels a and b), addition of ICI 182,780 abolished formation of endothelial cell-enriched spots while maintaining the MCF10A epithelium (FIG. 3, panel c).

Figure 5:
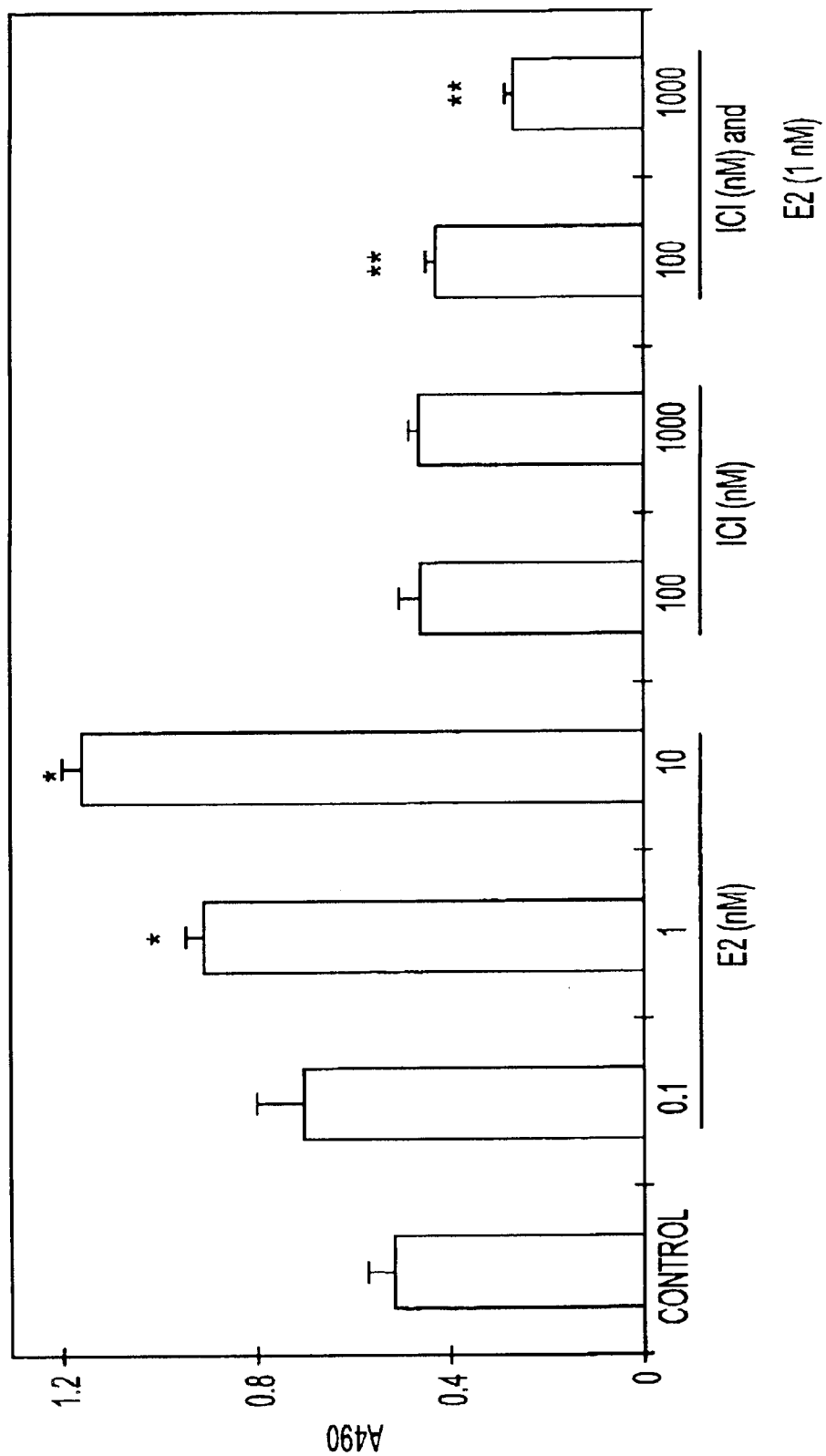
FIG. 5 is a graph showing regulation of 3D growth of EIII8-HUVEC cultures by estrogen. Growth was quantitated by MTS assay on day 5 of culture. Control wells received additions of vehicle (0.01% ethanol (v/v). Treatments included $E_2$ at 0.1, 1 or 10 nM; ICI182,780 at 100 or 1000 nM; and combinations of 1 nM $E_2$ with 100-fold or 1000-fold excess of ICI182,780. Results obtained from three independent experiments performed in triplicate are expressed as mean±S.E. * indicates doses of compounds that increased cell growth significantly over non-hormone-treated control (P<0.01). **Indicates doses of ICI182,780 that significantly decreased cell growth induced by $E_2$ (P<0.001).

3. Quantitative Assessment of Estrogen Effects on 3D Growth of Heterotypic (EIII8-HUVEC) Cultures Since exposure to $E_2$ significantly enhanced growth of EIII8 cells both in homotypic and heterotypic cultures (FIGS. 2 and 3), the inventors measured the effects of $E_2$ on cell proliferation in heterotypic 3D co-cultures by both MTS and trypan blue dye exclusion assays of dispase-treated cultures. According to both assays, $E_2$ elicited a dose dependent induction of growth at concentrations >1 nM; a 2-fold increase in growth over control cultures was observed with 10 nM $E_2$ ($p<0.01$; FIG. 5). This induction of growth by $E_2$ utilized the ER-dependent pathway, since the growth promoting effects of $E_2$ were abolished by 100-fold molar excess of the pure antiestrogen, ICI 182,780 ($p<0.001$; FIG. 5). Only the results of MTS assay are shown in FIG. 5, since results of both assays were in good agreement.

Figure 6:
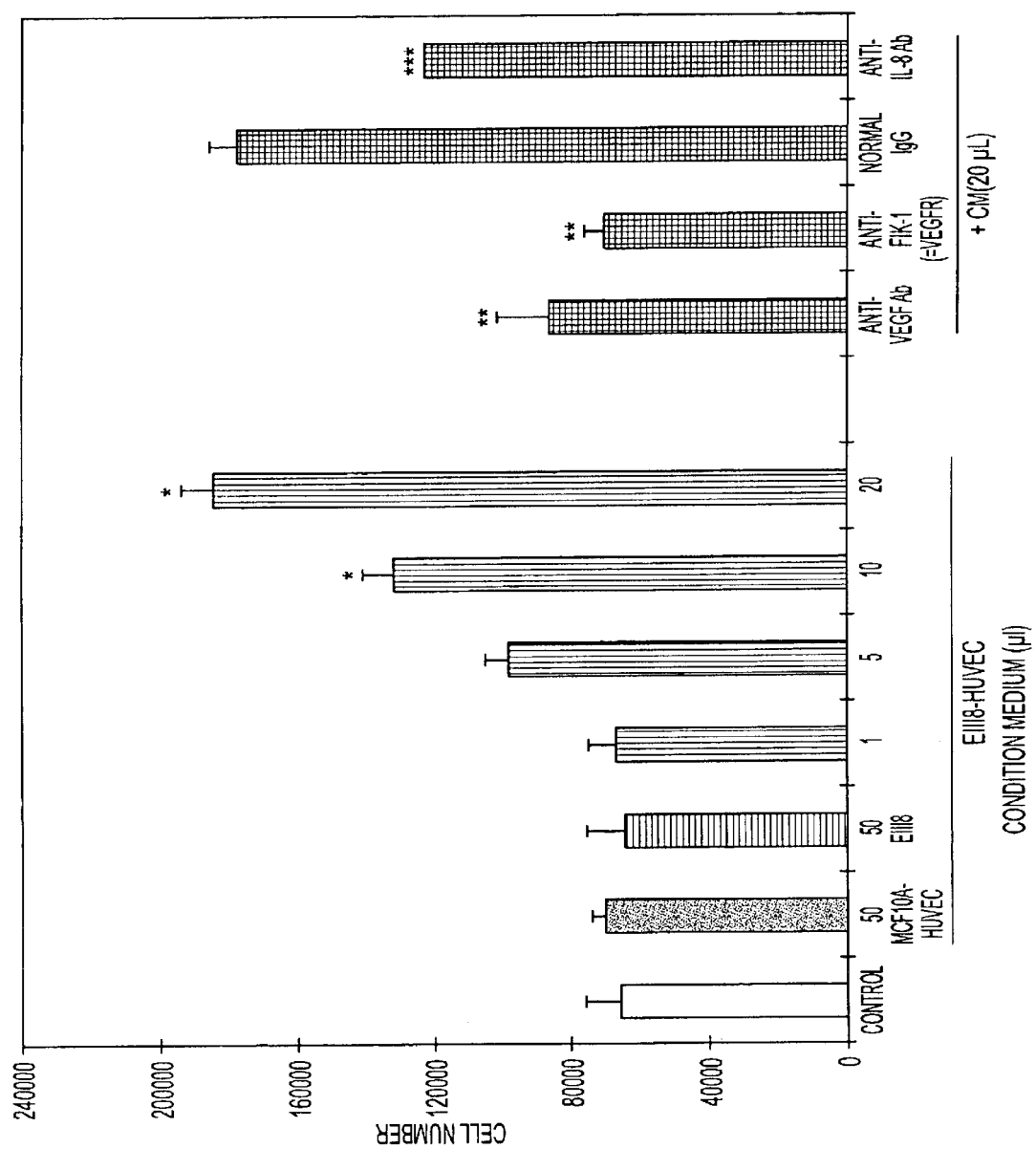
FIG. 6 is a graph showing the effect of conditioned medium (CM) from MCF10A-HUVEC, EIII8-HUVEC or EIII8 cultures on proliferation of HUVEC cells. HUVEC cells were treated with 50 µl or 1–20 µl of unconcentrated CM from EIII8, MCF10A-HUVEC, or EIII8-HUVEC cultures, respectively. Effects of antibodies on CM-induced HUVEC cell proliferation were tested in cultures treated with combination of 20 µl of CM from EIII8-HUVEC cultures and 10 µg/ml of anti-VEGF, anti-Flk-1 or anti-IL-8 antibodies, or an equivalent amount of mouse or rabbit normal IgG. Since no differences in cell numbers were observed between cultures treated with mouse or rabbit normal IgG, the results are grouped together. Results obtained from three independent experiments performed in triplicate are expressed as mean±S.E. * indicates cell proliferation that is significantly increased by CM from EIII8-HUVEC co-cultures over untreated control (P<0.001).  indicates a significant decrease in cell proliferation caused by anti-VEGF or anti-Flk-1 antibodies relative to cultures treated with normal IgG (P<0.001). *indicates significant decrease in cell proliferation induced by anti-IL-8 antibody as compared to cultures treated with normal IgG (P<0.02).
Figure 7A:
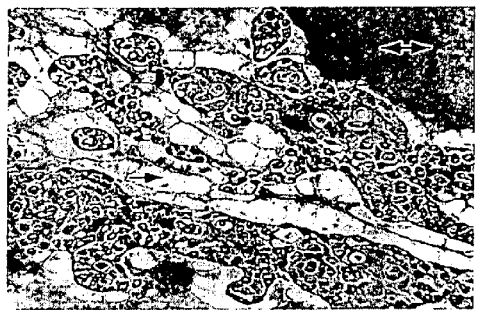
FIG. 7 shows formalin-fixed paraffin-embedded sections of EIII8-HUVEC 3D cultures were either stained with H&E (panel A) or with antibodies to PCNA (panel B), cytokeratins (panel C), muc-1 (panel D), cd31 (panel E), or Factor VIII (panel F). Staining was done on serial sections (though the sections look different). The inherent difficulty in obtaining identical serial sections is due in part to the small size and irregular growth of invading branching buds in Matrigel. Note the presence of numerous proliferating cells (panel B) in the finger-like projections or branching end buds that are invading the surrounding ECM with coincident ECM degradation (panels A and B). Arrows and double headed arrows, degraded ECM and intact ECM, respectively. Note the widespread immunoreactivity to cytokeratins (panel C) as compared to the localized distribution and membrane staining of cd31-positive (panel E) and factor VIII-expressing endothelial cells (panel F) that are denoted by arrows. MUC-1 staining (panel D) is predominantly localized in the lumen or lumen-forming areas of epithelium (arrows). Panels A, C, E and F are ×10; Panel D is ×4; and Panel B is ×25.
Figure 7B:
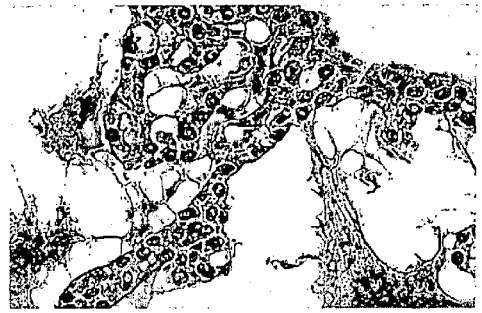
Figure 7C:
Figure 7D:
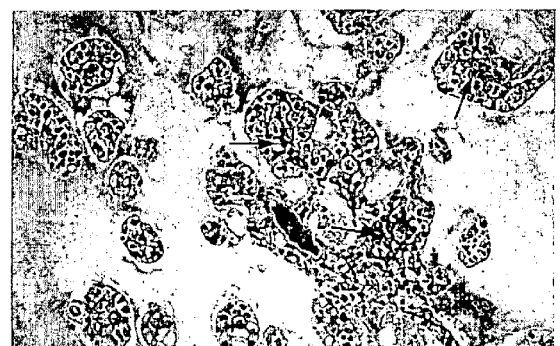
Figure 7E:
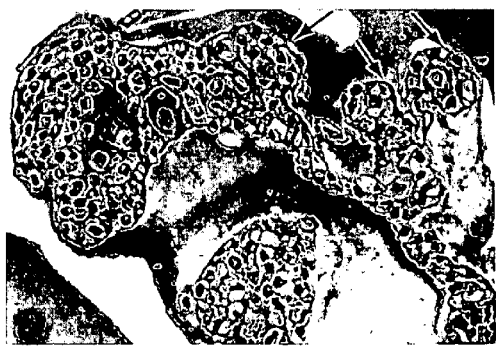
Figure 7F:

4. Conditioned Media from Heterotypic Co-Cultures Stimulated Growth of Endothelial Cell To determine if the stimulation of endothelial cell proliferation in EIII8-HUVEC co-cultures were due to soluble factor(s) secreted by EIII8 cells, the present inventors examined the effects of conditioned medium from homotypic (EIII8 or MCF10A) or heterotypic (EIII8-HUVEC or MCF10A-HUVEC) 3D cultures on HUVEC proliferation. Addition of up to 50 μl of homotypic EIII8 conditioned medium (FIG. 6), homotypic MCF10A conditioned medium, or heterotypic MCF10A-HUVEC conditioned medium (FIG. 6) did not result in growth stimulation of HUVEC compared to control cultures. In contrast, heterotypic EIII8-HUVEC conditioned medium elicited a significant dose-dependent induction of growth at volumes greater than 5 μl (p=0.02), and addition of 20 μl of conditioned medium elicited a 3-fold increase in HUVEC cell proliferation over that of control cultures (p<0.001; FIG. 6). These results indicate that secretion of growth stimulatory factor(s) into the culture media requires intimate interaction between epithelial and endothelial cells.

Since the cytokine, IL-8 (Polverini, P. J,. Crit. Rev. Oral Biol. Med. 6:230–247, 1995; Bar-Eli, M. *Pathobiology*, 67:12–8, 1999; Kumar, R. et al, Int. J. Oncol., 12:749–57, 1998; Miller, L. J. et al., Anticancer Res., 18:77–81, 1998), and the endothelial specific mitogen, VEGF, have been demonstrated to function as survival and anti-apoptotic factors for endothelial cells, the present inventors tested the effects of antibodies to VEGF, to VEGF receptor Flk-1/KDR, and to IL8 on conditioned medium-induced growth of HUVEC. Since expression of Flk-1/KDR is confined to endothelial cells, effects of neutralization of Flk-1/KDR with its antibody would indicate the selective nature of VEGF-induced mitogenesis. Addition of 10 μg/ml of antibodies to either VEGF or Flk-1/KDR abolished the conditioned medium-induced HUVEC proliferation (p<0.001). Addition of similar amounts of polyclonal anti-human IL8 antibody evoked only 40% inhibition of growth (p<0.02; FIG. 6). Inclusion of equivalent amounts of the corresponding normal IgG had no effect on conditioned medium-stimulated growth (FIG. 6). This inability of anti-IL-8 to cause greater inhibition of endothelial cell growth was not due to incomplete neutralization of IL8 in the conditioned medium since addition of higher amounts (up to 25 μg/ml) of anti-IL8 failed to increase the growth inhibition. These results suggest that, although IL8 is an important endothelial cell survival factor in these assays, it is not as potent as VEGF. Support for this assumption is also provided by the equally potent inhibition of growth by anti-Flk-1/KDR antibody as by VEGF antibody.

5. Heterotypic EIII8-HUVEC 3D Structures Express Epithelial and Endothelial Cell Function Markers Results shown in FIGS. 3, 4 and 6 clearly demonstrate that in heterotypic EIII8-HUVEC co-cultures, not only do both cell populations remain proliferative but there is a mutually beneficial intimate interaction between cell types. This is evident from the co-localization of branching ductal-alveolar outgrowths with endothelial cell-enriched spots (FIGS. 3 and 4). Histologic examination H&E stained, paraffin-embedded sections of 3D co-cultures revealed multi-layered epithelium at several regions of the tubular framework with branching end buds (finger-like projections) invading into the surrounding ECM with coincident ECM degradation (FIG. 7, panel A). Immunochemistry was used to confirm the proliferative potential of the 3D structures and to provide biochemical evidence for human breast epithelial cell and endothelial cell growth and function. The distribution of epithelial (cytokeratins, muc-1), endothelial (CD31, factor VIII-related antigen), and proliferation (PCNA) markers in 10-day old co-cultures was examined. While positive cytoplasmic immunoreactivity to pan-cytokeratins was observed in the majority of cells, as expected (FIG. 7, panel C), muc-1 glycoprotein expression was predominantly localized in the lumen or lumen-forming areas of epithelium (FIG. 7. panel D). These results confirm that the main tubular network is indeed comprised of human breast epithelial cells that, in 3D cultures, synthesize and secrete epimucin which is characteristic of epithelial glandular differentiation (Kufe, D. et al., Hybridoma, 3:223–232, 1984). In contrast to widespread distribution of cytokeratin immunoreactivity, reactivity to the endothelial cell marker, CD31 was restricted to areas on the tubular framework that probably correspond with endothelial cell-enriched spots (FIG. 7, panel E). Expression of Factor VIII-related antigen was localized to endothelial cell-enriched spots whereas the epithelial branching end buds in the immediate vicinity and in tubular framework were negative (FIG. 7, panel F). The majority of nuclei, particularly in the branching end buds, demonstrated positive nuclear immunoreactivity to anti-PCNA antibody, corroborating the high proliferative activity of the cells in the 3D structures (FIG. 7, panel B).

Figure 8A:
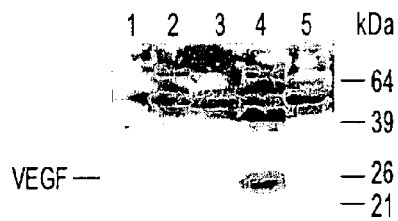
FIGS. 8A, 8B and 8C are a series of PAGE electropherograms and Western blots. 3-dimensional EIII8-HUVEC co-cultures show upregulated expression of $VEGF_{165}$, Flk-1, ER, IL-8, and MMP-2. 25 µg of protein present in culture media and corresponding matrix fractions were analyzed by Western blotting.
Figure 8B:
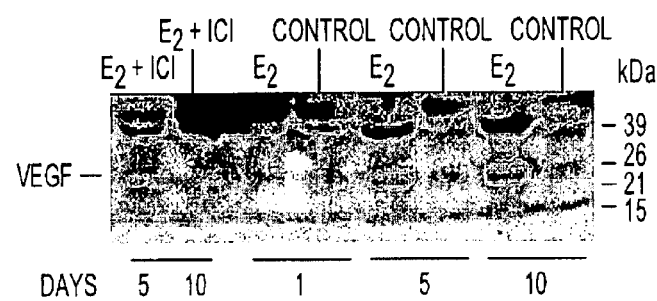

6. Expression of VEGF, IL-8, ER and Flk-1 Proteins is Upregulated in EIII8-HUVEC Co-cultures Unlike normal MCF10A cells, preneoplastic EIII8 cells provide a "good soil" for optimal survival, proliferation and functioning of endothelial cells, which appears to be facilitated at least in part by secretion of the endothelial cell growth stimulatory factors VEGF and IL-8 into the culture medium (FIG. 6). Densitometric analysis of the steady-state levels of VEGF protein in the culture medium of homotypic (EIII8, MCF10A or HUVEC) and heterotypic (EIII8-HUVEC or MCF10A-HUVEC) 3D cultures showed the presence of about 20-fold higher levels of $VEGF_{165}$ in culture medium of EIII8-HUVEC co-cultures when compared to corresponding fractions from homotypic EIII8 or MCF10A cultures, or heterotypic MCF10A-HUVEC co-cultures (FIG. 8A). Since the antibody used for Western analysis recognizes a C-terminal epitope present in $VEGF_{165}$, $VEGF_{189}$ and $VEGF_{206}$ but not in $VEGF_{121}$ (Neufeld et al., supra), alterations in relative levels of $VEGF_{121}$ have not been determined. Densitometric analysis of $VEGF_{165}$ in culture media of EIII8-HUVEC 3D cultures at various times revealed that while control samples maintain a constant level of $VEGF_{165}$ from days 1 to 10 of culture, treatment with 1 nM $E_2$ induced a 4- to 8-fold increase in $VEGF_{165}$ levels over those of control cultures by day 5 and 10 of culture, respectively (FIG. 8B). The role of estrogen in regulating VEGF expression became more by the blocking the $E_2$-stimulated increase in $VEGF_{165}$ levels by the pure antiestrogen, ICI 182,780 (at 100-fold molar excess over $E_2$); $VEGF_{165}$ returned to control levels (FIG. 8B).

Figure 8C:
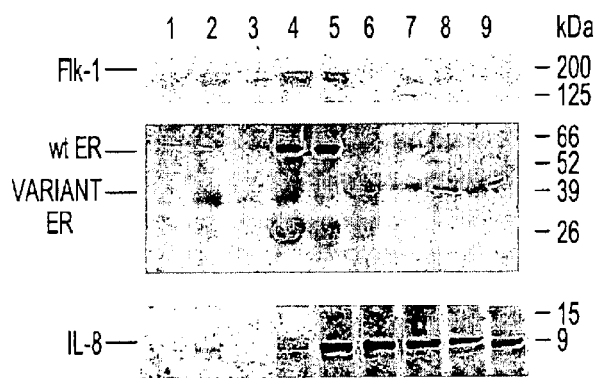

Analysis of IL-8 expression in the medium of HUVEC (FIG. 8C, lane 1) or MCF10A-HUVEC 3D cultures (FIG. 8C, lanes 2 and 3) showed the presence of only trace amounts. In contrast IL-8 levels were significantly up-regulated (>10-fold) in culture medium of corresponding 5- and 10-day old EIII8-HUVEC co-cultures (FIG. 8C, lanes 4 and 7). Interestingly, loss of IL-8 expression in 10-day old MCF10A-HUVEC co-cultures (FIG. 8C, lane 3) was coincident with loss of viability and stability of endothelial cell-enriched spots on MCF10A epithelium. In contrast to the inducing effects of estrogen on VEGF expression, $E_2$ did not appear to regulate IL-8 expression (FIG. 8C, lanes 5 and 8), and addition of 100-fold molar excess of the pure antiestrogen, ICI 182,780, had no effect on IL-8 levels (FIG. 8C, lanes 6 and 9).

Analysis of levels of Flk-1/KDR and ER proteins in the corresponding matrix fractions of homotypic (HUVEC) and heterotypic (MCF10A-HUVEC or EIII8-HUVEC) 3D cultures, revealed the presence of the endothelial cell-specific receptor, Flk-1/KDR, in HUVEC as well as in MCF10A-HUVEC and EIII8-HUVEC co-cultures (FIG. 8C). However, levels of Flk-1/KDR protein were significantly upregulated (about 12-fold) in 5-day old EIII8-HUVEC co-cultures (FIG. 8C, lane 4) over corresponding MCF10A-HUVEC co-cultures (FIG. 8C, lane 2) or homotypic HUVEC cultures (FIG. 8C, lane 1). Although levels of Flk-1/KDR protein in control and $E_2$-treated 5 day-old EIII8-HUVEC cultures appeared to be equally up-regulated (FIG. 8C, lanes 4 and 5), addition of ICI 182,780 at 100-fold molar excess of $E_2$ caused about 80% reduction in Flk-1/KDR protein levels (FIG. 8C, compare lanes 5 and 6). While the levels of $VEGF_{165}$ (FIG. 8B) and IL-8 (FIG. 8C) remained elevated in 5 and 10-day old EIII8-HUVEC cultures, Flk-1/KDR protein levels in 10-day old EIII8-HUVEC co-cultures declined by about 75% and were no longer regulated by $E_2$ or ICI 182,780 (FIG. 8C, lanes 7–9).

The pattern of expression of Flk-1/KDR protein parallels the expression pattern of ER in EIII8-HUVEC co-cultures. HUVEC are ER-positive (40), whereas MCF10A cells are ER-negative (41), and as expected, a constant level of wild type ER protein (67 kDa) probably originating from the HUVEC was detected both in homotypic HUVEC (FIG. 8C, lane 1) and heterotypic MCF10A-HUVEC 3D cultures (FIG. 8C, lanes 2 and 3). As observed in the case of Flk-1/KDR protein expression, levels of wild type ER protein were enhanced about 25-fold in heterotypic EIII8-HUVEC co-cultures relative to levels in HUVEC or MCF10A-HUVEC cultures (FIG. 8C, lanes 4 and 5). Treatment with ICI 182,780 at 100-fold molar excess over $E_2$, significantly reduced the amount of wild type ER with concomitant appearance of a 42 kDa protein that is immunoreactive with the anti-ER antibody (FIG. 8C, compare lanes 5 and 6). It is not yet clear whether the 42 kDa band (FIG. 8C, lanes 6–9) and the 26 kDa band (FIG. 8C, lanes 4 and 5) represent variant or truncated forms of ER (Murphy, L. C. et al., J. Steroid Biochem. Mol. Biol. 62:363–372, 1997). In 10-day old EIII8-HUVEC co-cultures, the 67 kDa wild type ER band is either undetectable or present in only trace amounts whereas the 42 kDa band represents the major immunoreactive ER band (FIG. 8C, lanes 7–9). It is not yet clear whether this shift in ER protein expression from 67 kDa to 42 kDa species reflects an alteration in hormonal sensitivity or responsiveness of the EIII8-HUVEC 3D cultures.

7. Expression of an Active Form of MMP-2 is Enhanced in EIII8-HUVEC Co-cultures

Figure 8D:
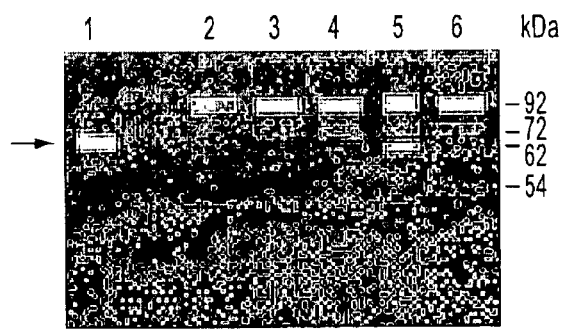
FIG. 8D is a gel zymogram of gelatinases secreted from HUVEC (lane 2), EIII8 (lane 3), MCF10A (lane 4), EIII8-HUVEC (lane 5) and MCF10A-HUVEC (lane 6) cultures. Lane 1 represents activated MMP-2 used as positive control. Conditioned media prepared from 5 day-old EIII8, MCF10A, EIII8-HUVEC or MCF10A-HUVEC cultures, or at 2 days of HUVEC cell cultures were analyzed on gelatin-embedded substrate gels. Arrow: position of the active form of MMP-2. The gels are representative of three independent experiments.
Figure 9A:
FIG. 9 is a photomicrograph showing whole mounts of 3-dimensional EIII8-HUVEC co-cultures grown in Matrigel. Cultures were fixed in buffered formalin and stained with 0.25% toluidine blue. Note the presence of ductal-alveolar outgrowths (clusters) that are formed de novo from single EIII8 cells. These structures are formed only when EIII8 cells are co-cultured with HUVEC or with breast fibroblasts. Since these structures are very small, and since the ductal outgrowths invade into different levels of the matrix, it is difficult to obtain a complete picture as several outgrowths are out of focus at any given plane.
Figure 9B:
Figure 10A:
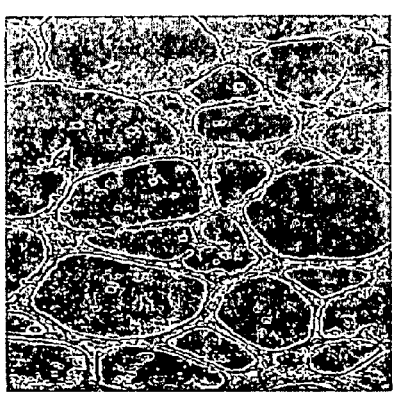
FIG. 10 (Panels A–H) is a set of photomicrographs showing phase contrast morphology of homotypic and heterotypic 3D Matrigel cultures. Panels A and E: MCF10A and EIII8, respectively; Panels B and F, MCF10A+31R and EIII8+31R, respectively; Panels C and D, MCF10A+31R+HUVEC and EIII8+31R+HUVEC, respectively, at 10 days of culture. Panels D and H, 31R fibroblasts from normal breast tissue (reduction mammoplasty) and HUVECs, respectively at 10 and 3 days of culture. Note the difference in morphologies between homotypic (MCF10A, EIII8, HUVECs) and heterotypic cultures containing fibroblasts. Magnification, ×100 (panels A, E, H); Bar, 40 μm (panels B, C, D, F, G).
Figure 10B:
Figure 10C:
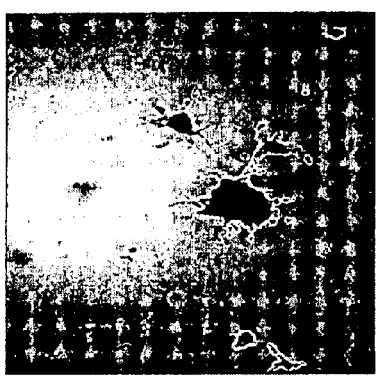
Figure 10D:
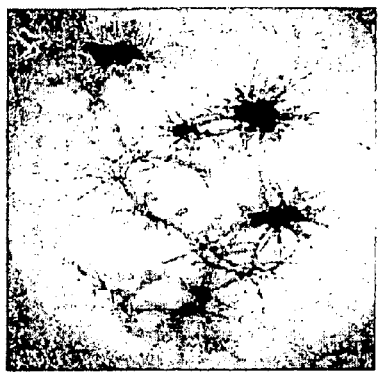
Figure 10E:
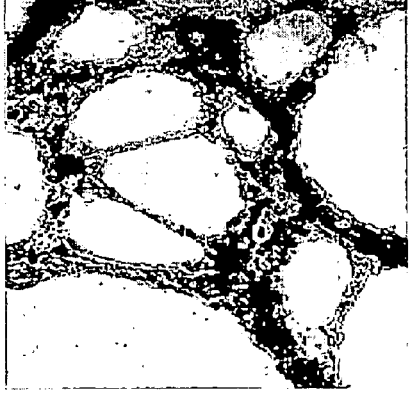
Figure 10F:
Figure 10G:
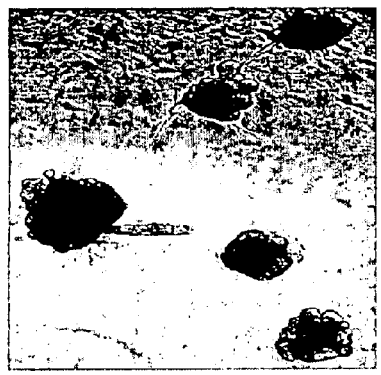
Figure 10H:
Figure 11A:
FIG. 11 (Panels A–F) is a set of photomicrographs showing phase contrast morphology of heterotypic 3D Matrigel cultures containing breast tumor-derived fibroblasts in the presence or absence of HUVECs. Panels A, B: MCF10A+38T or MCF10A+38T+HUVEC, respectively; Panels C and D: EIII8+38T or EIII8+38T+HUVEC, respectively; Panels E and F: EIII8+12T or EIII8+12T+HUVEC, respectively. Note the difference in the morphologies of the 3D structures formed between MCF 10A and EIII8 cells with tumor derived fibroblasts. Also note the dramatic increase in proliferation and branching ductular-alveolar morphogenesis induced in EIII8+38T and EIII8+12T cultures upon inclusion of HUVECs. Bar, 40 μm.
Figure 11B:
Figure 11C:
Figure 11D:
Figure 11E:
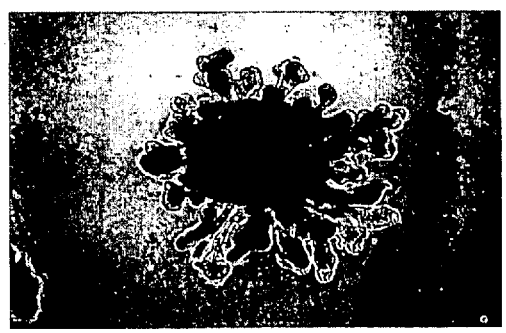
Figure 11F:
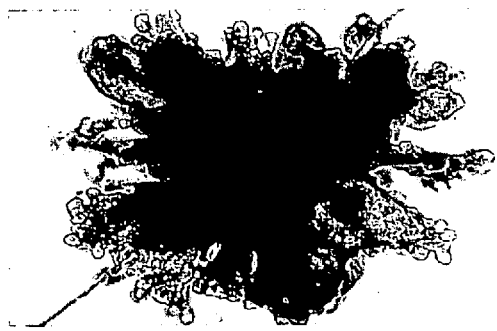

Degradation and remodeling of ECM are essential processes for angiogenesis and involve the matrix metalloproteinase/tissue inhibitor of metalloproteinases (MMP/TIMP) family of proteases (Moses, M. A. et al., Science 248:1408–1410, 1990; Mignatti, P et al., J. Cell Biol., 108:671–682, 1988; Johnson, M. D. et al., J. Cell Physiol.,160:194–202, 1994). MMP-mediated matrix remodeling also appears to promote the growth of tumor cells, possibly by facilitating the proliferation and migration of endothelial cells and the neovasculature of tumor tissue (Ingber, D. E. Cancer Biol., 3:57–63, 1992). In the presence of endothelial cells, EIII8 cells acquired the ability to invade and degrade the surrounding ECM (FIG. 7, panel a). MMPs including MMP-2 (Gabrisa, S. et al., Cancer Res., 47:1523–1528, 1987; Liotta, L. A. et al., J. Natl. Cancer Inst., 81:556–557, 1989) and MMP-9 (Bernhard, E. J. et al., Cancer Res., 50:3872–3877, 1990; Okada, Y. et al., Biophys. Res. Commun., 1 71:610–617, 1990) play major roles in degradation of ECM in tumor invasion. In order to identify the gelatinolytic activity of 3D cultures, the inventors performed gelatin zymography of conditioned medium from homotypic (HUVEC, EIII8 or MCF10A) and heterotypic (EIII8-HUVEC or MCF10A-HUVEC) cultures. While the latent or pro-form of MMP-2 (72 kDa) was detected at low levels in all samples, the active form of MMP-2 (62 kDa) was present at significantly elevated levels only in the conditioned medium of EIII8-HUVEC co-cultures (FIG. 8D, lane 5). No difference in the amounts of proteins corresponding to 92 kDa (MMP-9) and 96 kDa bands was observed (FIG. 8D). This lack of regulation of MMP-9 levels suggests either the presence of contaminating MMP-9 that is secreted from Matrigel during culture (Schnaper, H. W. et al, J. Cell Physiol., 166:235–246, 1993) or a less important role for MMP-9 in interactions between EIII8 and HUVEC cells in this system.

8. Discussion

Despite wide agreement about the involvement of estrogen in the etiology of breast cancer, there is uncertainty as to its precise role(s) in the biology of breast cancer development. The foregoing Example describes an in vitro assay system that allows exploration of the interactions between human breast epithelial cells and endothelial cells on reconstituted basement membrane, and shows that distinct patterns of angiogenesis permit discrimination between normal (or benign) and premalignant mammary epithelial cells.

Results from this study show that estrogen exerts a direct and early effect on mammary carcinogenesis by stimulating proliferation of both endothelial cells (an important stromal component) and premalignant epithelial cells.

This model system is distinct from those reported by others in that morphogenesis of ductal-alveolar units resembling terminal ductal lobular units occurs de novo (from single cells) rather than from organoids of primary cultures or simple organization from single cells into spherical structures with acini.

When normal MCF10A or preoplastic EIII8 cells are co-cultured with HUVEC on a layer of Matrigel, all cell types in both co-cultures rapidly organize into interconnected tubes with the endothelial cells preferring to grow on the epithelium. Although further differentiation of endothelial cells into complex 3D networks is observed in both MCF10A- and EIII8-HUVEC co-cultures, stable and sustained proliferation of endothelial networks is observed only in EIII8-HUVEC co-cultures. Although the endothelial cells grow on top of epithelial cells, stable and functional 3D vascular networks (established by Factor VIII expression) develop only at specific sites on the EIII8 epithelium. The occurrence of 3D vascular networks at specific sites may be induced by a subpopulation of EIII8 cells (with morphological, genetic or functional alterations) that are committed progenitors of cancers. This is possible since like its parental line, MCF10AT1 (Shekhar et al, supra), lesions arising from EIII8 cells in immunodeficient mice exhibit a heterogeneous spectrum of advanced histological grades of progression (atypical hyperplasia, CIS and invasive carcinoma) besides simple ducts, with prominent angiogenesis. The inability of normal MCF10A cells to sustain stable 3D vascular networks in vitro is consistent with their inability to produce persistent lesions in immunodeficient mice (Miller et al, 1993, supra).

The onset of malignancy is an active process that requires reciprocal paracrine interactions between endothelial and tumor cells (Rak, J. et al., Eur. J. Cancer, 32A:2438–2450, 1996). Data from the present in vitro model exemplify the need, at a very early stage, for close, cooperative paracrine interactions between preoplastic mammary epithelial cells and endothelial cells in the generation of both an angiogenic response and ductal-alveolar morphogenesis. Preoplastic breast epithelial cells facilitate active proliferation and development of stable endothelial cell-derived 3D vascular networks via soluble angiogenic factors such as VEGF and IL-8, and the 3D vascular networks or sustained angiogenesis in turn assist in generation of local ductal-alveolar outgrowths.

Although sustained angiogenesis induces formation of alveolar outgrowths, an indicator of mammary glandular differentiation (characterized morphologically and by muc-1 expression), these outgrowths are not normal as they have tremendous potential to proliferate and invade/degrade the surrounding ECM. As no productive interactions occur between MCF10A and endothelial cells, the findings above indicate that the epithelial cell background plays a major role in expression and maintenance of the angiogenic phenotype.

One of the factors contributing to the observed differences in angiogenic response between normal MCF10A and preneoplastic EIII8 cells may be the presence of activated Ha-ras in the latter (Basolo et al., supra). Previous studies indicated that the angiogenic switch in ras-transformed cells may be physiologically promoted by the tumor microenvironment through induction of the angiogenic mitogen, VEGF (Bouck, N, Cancer Cells, 2:179–185, 1990; Bouck, N, In: Benz et al., (eds), Oncogenes and Tumor Suppressor Genes in Human Malignancy, pp. 359–371, Boston: Kluwer Academic, 1993). Although the present results support the role of activated ras in sustaining angiogenesis, it is clearly not sufficient since all MCF10AT cells stably express activated ras, yet the development of stable 3D vascular networks occurs only at specific sites on the EIII8 epithelium.

Another important difference between MCF10A and MCF10AT cells that may contribute to differences in angiogenic response is the expression of functional wild type ER in MCF10AT cells (Shekhar, P. V. M. et al., J. Natl. Cancer Inst., 89:1774–1782, 1997; Shekhar, P. V. M. et al., Int. J. Oncology, 13:907–915, 1998) and its absence in MCF10A cells (Soule et al., supra; Pilat, M. J. et al., Breast Cancer Res. Treat., 37:253–266, 1996). An earlier study from the present inventor's laboratory showed that estrogen enhanced preneoplastic progression of MCF10AT1 cells in vivo as lesions of MCF10AT1 (Shekhar et al., Am. J. Pathol., 1998, supra). These as well as EIII8 cells harvested from estrogen-supplemented animals exhibited rapid growth and advanced histological grades of progression with prominent angiogenesis as compared to simple or moderate hyperplasia without atypia or angiogenesis in control unsupplemented animals (Shekhar et al., supra). The importance of estrogen in regulation of the angiogenic response in vivo is recapitulated in the present model system, since estrogen specifically stimulates growth of both 3D vascular networks and ductal-alveolar outgrowths, and these processes are blocked or significantly inhibited by the pure antiestrogen, ICI 182,780.

Endothelial cells possess ER (Kim-Schulze et al., supra), and estrogen increases endothelial cell proliferation (Johannisson, E. et al., Hum. Reprod., 1:207–212, 1986). In the present system, much of the $E_2$/ER-mediated effects on angiogenesis appear to emanate from its stimulatory effects on expression of angiogenesis regulating factors, VEGF and the VEGF receptor, Flk-1/KDR (=VEGFR-2). These findings are consistent with previous reports that estrogens influence VEGF/PF mRNA expression in the uterus (Cullinan-Bove, supra), and in the well-vascularized, DMBA-induced hormone-dependent rat mammary tumors (Kaidoh, T. et al., Virchows Arch. Pathol. Anat. 418:111–117, 1991). M. Fukeda et al., Basic Appl. Histochem. 29:21–43, 1985) observed that the growth of capillary endothelial cells in DMBA-induced tumors was estrogen-dependent, and that treatment of DMBA-exposed rats with $E_2$ after ovariectomy prevented tumor necrosis and maintained high rates of endothelial cell proliferation. Similarly, estrogen-induced angiogenesis in rat pituitary tumors is associated with $E_2$-mediated increases in the expression of both ligand, VEGF and its receptor, Flk-1/KDR, suggesting an important role for estrogen in the initial step of angiogenesis regulation (Banerjee, S. K. et al., Carcinogenesis 18:1155–61, 1997). In contrast to effects of estrogen on VEGF and Flk-1/KDR expression in the present system, steady-state levels of IL-8, an important endothelial cell survival factor, are unaffected by estrogen and remain elevated through out the culture period.

In 10-day old cultures, high levels of IL-8 and $VEGF_{165}$ proteins are maintained, whereas Flk-1/KDR protein levels are significantly reduced, though maintained at a steady level that is unaffected by estrogen or ICI 182,780. This alteration in regulation of Flk-1/KDR protein is correlated with a dramatic downregulation in levels of the 67 kDa wild type ER and concomitant appearance of a prominent 42 kDa anti-ER immunoreactive protein. It remains to be established whether the 42 kDa protein represents a form of variant ER or is simply a protein that cross-reacts an N-terminus epitope-specific anti-ER antibody.

Numerous studies have reported the detection by RT-PCR of ER mRNA splice variants in normal and cancerous human breast tissues, the biological and clinical significance of which might be significant. However, the existence of these variants at the protein level has yet to be established (Dowsett, M. et al., Eur. J. Cancer, 33:1177–1183, 1997; Tonetti, D. A. et al., J. Steroid Biochem. Mol. Biol., 62:119–128, 1997). Such a shift in ER status, coupled with alterations in sensitivity of Flk-1/KDR expression to estrogen and ICI 182,780 may signify a switch from an estrogen-responsive to an estrogen-insensitive phase of angiogenesis and mark the beginning of new autonomous growth.

Expression of angiogenic activity is a predictable property of many preneoplastic cells and may represent one of the earliest indication that a cell population has become committed to malignancy (Folkman, J., Adv. Cancer Res., 43:175–203, 1985). Results from the present novel in vitro model system reinforces the concept that like tumor cells, preneoplastic human breast epithelial cells actively produce diffusible angiogenic factors and cytokines that directly activate endothelial cells stimulating them to sprout and initiate development of 3D vascular networks which in turn induce development of ductal-alveolar outgrowths with capacity to invade and degrade the surrounding ECM. The characteristic expression of activated MMP-2 observed only in preneoplastic EIII8-HUVEC co-cultures fortifies the importance of proteolytic enzymes in the release of angiogenic factors sequestered in ECM (Vlodavsky, I. et al. J. Cell Biochem., 47:167–176, 1991; Vlodavsky, I. et al., Trends Biochem. Sci., 16:268–71, 1991). The direct correlation observed between growth and development of vascular networks and ductal-alveolar outgrowths with coincident ECM remodeling suggests that increased gelatinolytic activity secreted by epithelial and/or endothelial cells may facilitate release of angiogenic growth factors locally from ECM.

In summary, the foregoing Example describes a novel, physiologically relevant in vitro model system that not only recapitulates several important aspects of estrogen-induced growth and preneoplastic progression of MCF10AT1 cells in vivo, but also demonstrates for the first time the integral role endothelial cells play in ductal-alveolar morphogenesis and proliferation of preneoplastic human breast epithelial cells. This assay system will provide a unique tool to explore systematically the expression of growth regulatory molecules that determine epithelial cell-specific and endothelial cell-specific requirements for angiogenesis and progression of preneoplastic breast disease.

EXAMPLE III

Studies of 3D Co-Cultures Involving Breast Epithelial Cells, Breast Fibroblasts and Endothelial Cells 1. Heterotypic Co-Culture of Fibroblasts from Normal or Tumor Tissue with MCF10A or EIII8 Cells Cause Dominant Growth Inhibitory and Stimulatory Effects, Respectively, of the Human Breast Epithelial Cells.

The present inventors compared the effects of normal fibroblasts and tumor derived human breast fibroblasts in initiating, supporting and maintaining 3-D organization and growth of MCF10A and EIII8 cells. Homotypic culture of MCF10A or EIII8 cells produce tubular networks (FIG. 10, panels A and E; see also Example II). In contrast, MCF10A or EIII8 cells seeded on Matrigel in contact-dependent co-cultures with fibroblasts derived from reduction mammoplasty or breast tumor tissues produce sealed structures consisting of centrally located fibroblasts with epithelial buds emerging from the central fibroblast core (FIGS. 10 and 11).

When co-cultured with MCF10A or EIII8 cells, reduction mammoplasty fibroblasts 31R or 14R retained their capacity for chemotaxis but were unable or only weakly able to support growth and differentiation of MCF10A and EIII8 cells, respectively (FIG. 10, panels B and F). In contrast co-cultures of MCF10A or EIII8 cells with 12T tumor-derived (or 12B benign), or 38T tumor-derived (or 38B benign) breast fibroblasts, besides concentrating cells by chemotaxis, induced growth and ductal-alveolar morphogenesis of both MCF10A and EIII8 cells (FIG. 11, panels A, C and E). However, a principal difference between the MCF10A and EIII8 cultures was the formation of a larger number of highly proliferative, ductal-alveolar units with EIII8 cells as compared to those formed by MCF10A cells (FIG. 11, compare panel A with C and E). These results indicate major differences in the ability of fibroblasts derived from reduction mammoplasty versus benign or tumor breast tissues to support the growth and morphogenesis of normal and preneoplastic breast epithelial cells.

Inclusion of HUVECs in MCF10A co-cultures with fibroblasts from either reduction mammoplasty or benign/tumor tissues (FIG. 10, panel C, and FIG. 11, panel B), or EIII8 co-cultures with reduction mammoplasty fibroblasts (FIG. 10, panel G) failed to alter the growth characteristics induced by fibroblasts. In contrast, the inclusion of HUVECs into EIII8 co-cultures with fibroblasts from benign/tumor tissues (12B, 12T, 38B or 38T) resulted in a dramatic (FIG. 11, panels D and F) induction of branching ductal-alveolar morphogenesis. These results are consistent with the results of Example II (see also Shekhar et al., supra) that, unlike normal MCF10A cells, preneoplastic EIII8 cells have the capacity to support endothelial cell survival and growth. Similar co-cultures set up with HT1080 fibrosarcoma cells, normal IMR-90 lung or embryonal NIH 3T3 fibroblasts failed to elicit similar effects on breast epithelial growth and morphogenesis as those induced by human breast fibroblasts.

2. Quantitative Evaluation of the Effects of Fibroblasts and Endothelial Cells on 3D Growth of EIII8 Cells, and its Responsiveness to Estrogen.

Figure 12:
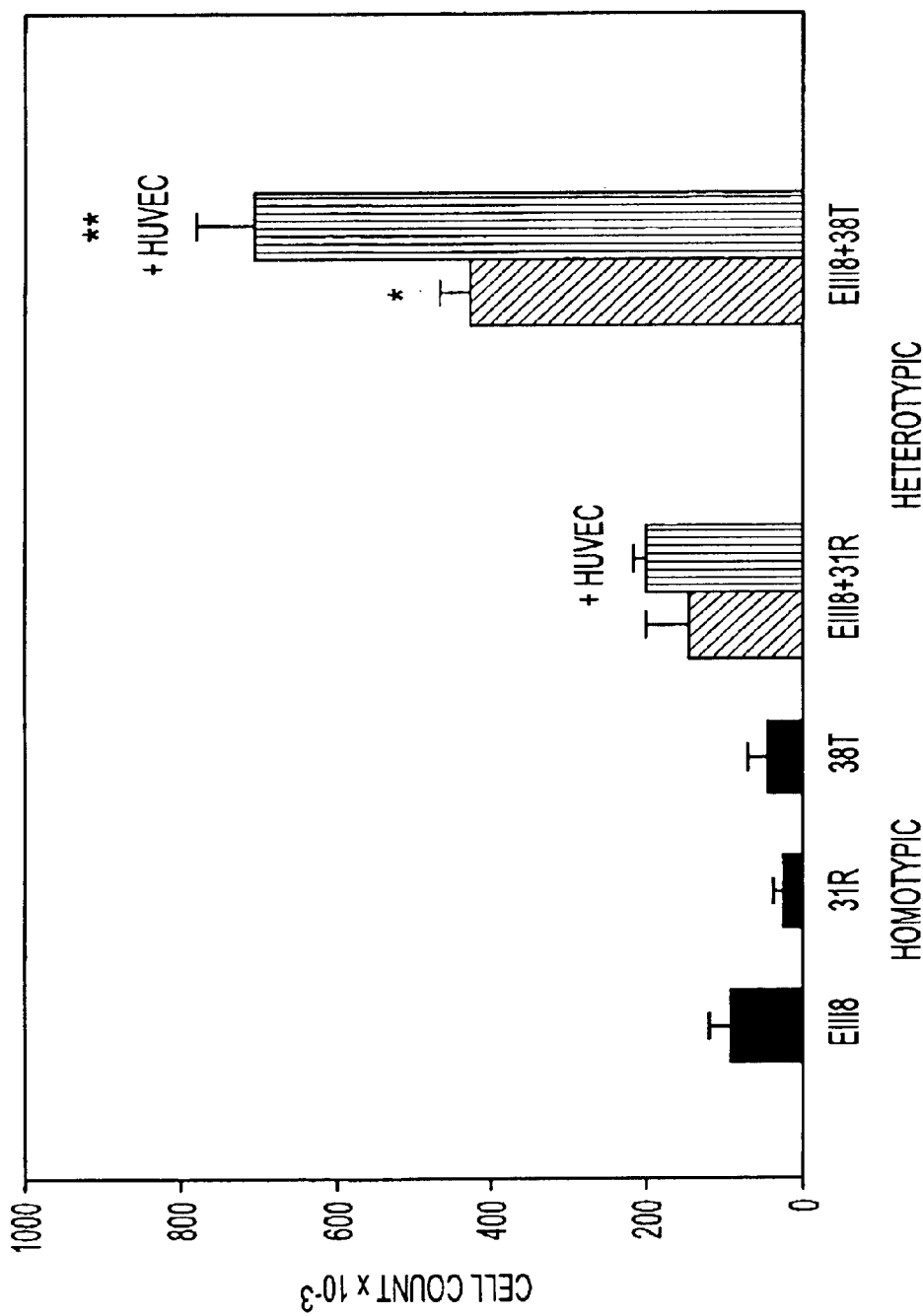
FIG. 12 is a histogram showing the regulation of 3Dd growth of EIII8 cells by breast fibroblasts derived from reduction mammoplasty or from tumors, and endothelial cells. Growth was quantitated by direct counting of viable cells from dispase-treated Matrigel cultures at 6 days. Cell counts for homotypic HUVECs are not shown as no viable cells remained at 6 days of culture. Results obtained from 3 independent experiments are expressed as mean±S.E. * Indicates significant increase in cell growth over heterotypic EIII8+31R ($p<0.001$); **indicates significant increase in cell growth over EIII8+31R+HUVEC ($p<0.005$).

Since the results shown in FIGS. 10 and 11 revealed remarkable differences in the abilities of fibroblasts from reduction mammoplasty and breast tumor tissues to mediate 3D organization and morphogenesis of EIII8 cells and further induction by ECs, the present inventors measured cell growth in homotypic (EIII8, 31R, 38T, HUVEC) and heterotypic (EIII8+31R, EIII8+38T) co-cultures, both in the presence and absence of ECs, by direct cell counting of viable cells from dispase-digested Matrigel. Consistent with the visual effects on growth and morphology of the co-cultures observed in FIGS. 10 and 11, contact dependent co-culture of EIII8 with 38T tumor-derived breast fibroblasts elicited a 3-fold increase in growth (p<0.001) over corresponding cultures with 31R reduction mammoplasty fibroblasts (FIG. 12). Inclusion of HUVEC into EIII8+38T co-cultures caused further enhancement of cell proliferation, ~1.7-fold higher (p<0.01) than EIII8–38T co-cultures, and ~3.5-fold higher (p<0.005) than EIII8+31R+HUVEC tricultures. These findings were not unique to 38T or 31R fibroblasts, as similar effects on growth were observed with 12T tumor-derived fibroblasts, or 14R reduction mammoplasty fibroblasts.

Figure 13:
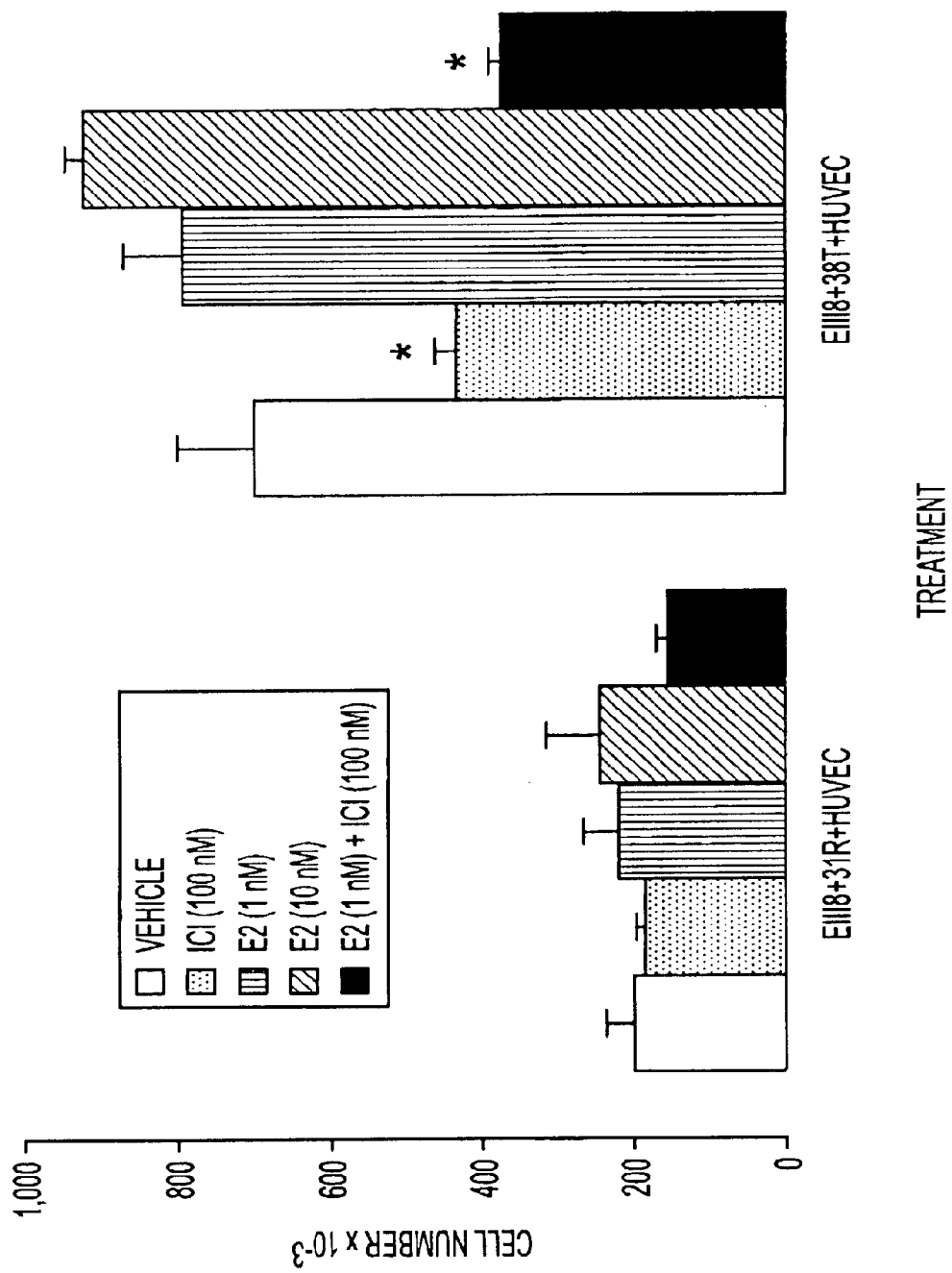
FIG. 13 is a histogram showing the regulation of 3D growth of EIII8+31R+HUVEC and EIII8+38T+HUVEC cultures by estrogen. Growth was quantitated at 6 days of culture as described for FIG. 12. Control wells received vehicle (0.01%, v/v ethanol). Treatments included $E_2$ at 1 or 10 nM; ICI 182,780 at 100 nM; and combination of 1 nM $E_2$ with 100-fold excess of ICI 182,780. Results obtained from 3 independent experiments are expressed as mean±S.E. *Indicates doses of ICI 182,780 that significantly decreased cell growth in vehicle- and $E_2$-treated cultures ($p<0.001$).
Figure 14A:
FIG. 14 (Panels A–H) is a set of photomicrographs showing formalin-fixed EIII8+12T 3D cultures were either whole mounted (panels A and B) or paraffin-embedded and stained with H&E (panels C and D) or with antibodies to Ki-67 (E), cytokeratins (F), muc-1 (G), or vimentin (H). Note the presence of a distinct central stromal core (positive for vimentin, panel H) around which the emerging epithelial buds (cytokeratin-positive, muc-1-positive, panels F and G, respectively) are arranged. Also note the presence of numerous Ki-67-positive nuclei in the epithelial buds and their absence in the fibroblast core. Magnification, panels A, E–H, ×10; B and D, ×25; C, ×4.
Figure 14B:
Figure 14C:
Figure 14D:
Figure 14E:
Figure 14F:
Figure 14G:
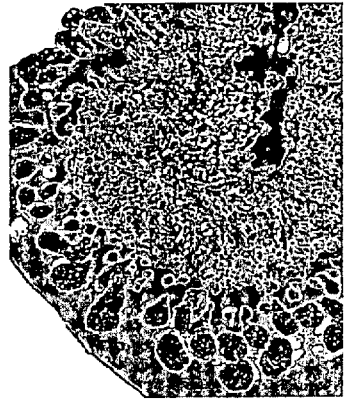
Figure 14H:
Figure 15C:
FIG. 15 (Panels A–I) is a set of photomicrographs showing formalin-fixed, paraffin-embedded sections of EIII8+12T+HUVEC 3D cultures were stained with antibodies to cd31 (panels A and B), Factor VIII (panels C and D), MMP-9 (E and F), VEGF (G), VEGF receptor-2 (H), or $\alpha_v\beta_3$-integrin (I). Arrows indicate localization of cd31 and Factor VIII immunoreactivity at the base of epithelial outgrowths (A and D) and in the stromal core but close to the base of epithelial buds (B and C). Note the presence of coincident ECM degradation (cleared Matrigel) in the immediate vicinity of the three dimensional growth (that is absent in EIII8-12T cultures, FIG. 14) and the presence of intense reactivity to MMP-9 antibody (white arrow) in the immediate vicinity of the epithelial outgrowths (E and F). Arrows and double headed arrow indicates the cleared Matrigel and intact Matrigel, respectively. Note the presence of intense immunoreactivity to VEGF antibody in the epithelial region (G, solid arrow) as compared to the focal reactivity observed in the stromal core (thin arrow). Localization of VEGF in the stromal core is similar to that observed with VEGF receptor-2 (H, arrow) or $\alpha_v\beta_3$-integrin (I, arrow) antibodies. Magnification, panels A, B, C, E, G, ×4; D, H, I, ×10; F, ×40.
Figure 15F:
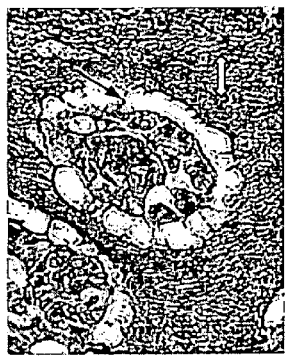
Figure 15I:
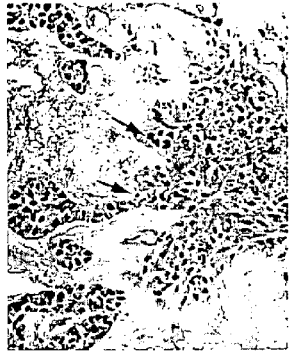
Figure 15B:
Figure 15E:
Figure 15H:
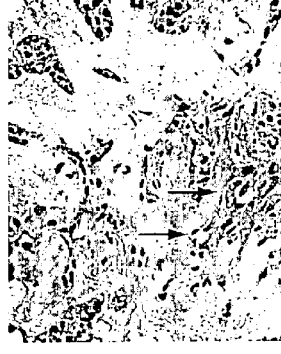
Figure 15A:
Figure 15D:
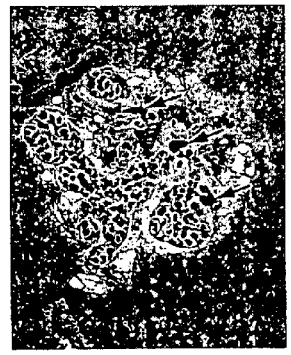
Figure 15G:

Since EIII8 cells respond to $E_2$ treatment with pronounced growth enhancement (Example II), the effects of 17 $\beta$-$E_2$ on growth of EIII8-fibroblast-endothelial tricultures were evaluated in order to determine if maintenance of close contact with breast fibroblasts influenced responsiveness of EIII8 cells to $E_2$. Treatment of EIII8 tricultures containing reduction mammoplasty fibroblasts with either 1 or 10 nM $E_2$ failed to stimulate growth (FIG. 13). Similar treatment of EIII8 tricultures containing 38T tumor-derived breast fibroblasts invoked only a marginal increase in growth (p<0.03) that was apparent only with 10 nM $E_2$ (FIG. 13).

However, the inductive effects of exogenous $E_2$ became more obvious upon addition of the pure estrogen antagonist ICI 182,780 which significantly inhibited (p<0.001) growth in both vehicle- and $E_2$-treated cultures (FIG. 13). As no $E_2$-mediated stimulatory effects were observed in EIII8 co-cultures containing reduction mammoplasty fibroblasts, these results suggested that the $E_2$-induced growth effects observed in vehicle-treated EIII8+38T+HUVEC tricultures were not due to contaminating estrogen or estrogenic compounds in the phenol red-free culture medium but probably originated from the tumor-derived fibroblasts. From these results, the inventors inferred that breast fibroblasts play a dominant role in the maintenance and induction of epithelial growth and morphogenesis. On the one hand, fibroblasts from normal breast tissues are growth inhibitory and can override genetic constraints imposed by preneoplastic breast epithelial cells. On the other hand, tumor-derived breast fibroblasts provide a growth stimulatory influence that can overcome or augment the genetic constraints imposed by normal or preneoplastic breast epithelial cells, respectively.

3. Contact Dependent Coexistence with Tumor-Derived Breast Fibroblasts Facilitates Structural and Functional Organization that Mimics the In Vivo Situation.

Results shown in FIGS. 10–13 demonstrate that benign- or tumor-derived breast fibroblasts exert inductive branching morphogenic effects on preneoplastic EIII8 cells that is further enhanced by the presence of ECs. Histological analysis of H&E-stained paraffin-embedded EIII8 co-cultures revealed the presence of a central core of fibroblasts from which, and around which, branching epithelial buds emerge (FIGS. 14 and 15) confirming the results seen in the whole mount (FIG. 14, panel A) and phase contrast microscopy (FIGS. 10 and 11).

Further confirmatory biochemical evidence for the localization and functionality of epithelial, fibroblast and endothelial components was obtained by immunochemical analysis of expression of relevant markers: cytokeratins and muc-1 (epithelial), vimentin (fibroblast), cd31, Factor VIII, VEGF receptor-2, and $\alpha_v\beta_3$ integrin (endothelial cells). Results in FIG. 14 show that the majority of the cytokeratin-positive, muc-1 expressing epithelial cells (panels F and G)

were organized as buds around the central vimentin-positive fibroblast core (panel H) whereas a small fraction of epithelial cells are retained in the stromal core (panels F and G). This residual epithelial cell population may represent "fragments of ducts emerging from the core" or cells that did not participate in the organization process. The epithelial structures exhibited pronounced branching and increased potential to invade and degrade the coincident ECM in EIII8 co-cultures containing endothelial cells (FIG. 15, panel A).

This ability to degrade the ECM is consistent with the strong reactivity to MMP-9 antibody in the immediate vicinity of epithelial buds in EIII8+12T+HUVEC tricultures (FIG. 15, panels E and F). The ability of epithelium to invade and proteolytically degrade the surrounding ECM required the presence of endothelial cells, as EIII8 co-cultures containing only benign- or tumor-derived fibroblasts lacked this property.

It is interesting to note that the central fibroblast core in EIII8 co-cultures was nonproliferating in contrast to the high Ki-67 labeling of epithelial buds (FIG. 14, panel E), suggesting that the metabolically active yet nonproliferating fibroblasts can serve as a sufficient structural platform for maintenance and support of epithelial survival, growth and morphogenesis (FIG. 14).

An interesting feature observed in the EIII8 tricultures was the establishment of contact between epithelial, fibroblast and endothelial cells that is most suitable for paracrine interaction. In EIII8+12T+HUVEC tricultures, the cd31-positive factor VIII-expressing endothelial cells were situated in the central stromal core but predominantly close to the base of the branching epithelial buds (FIG. 15, panels A–D). These vascular units were functional as they not only expressed factor VIII but were also positive for the endothelial-specific VEGF receptor-2 (Flk-1) and ($\alpha_v\beta_3$) integrin, markers indicative of active angiogenesis (FIG. 15, panels H and I).

The maintenance of endothelial cell survival and growth appears to be ensured by the large amounts of VEGF expressed and secreted by EIII8 epithelium (observed as intense immunoreactivity to VEGF antibody in the epithelial compartment) whereas only focal immunostaining to VEGF antibody (that is similar to staining patterns of Flk-1 and $\alpha_v\beta_3$ integrin) was observed in the central stromal core (FIG. 15, panel G).

8. Discussion

Several studies have shown that stroma is a key determinant of epithelial proliferation (Sialg, P. et al., Science, 230: 669–672, 1985), cell death (Kratochwil, K., J. Pathol., 149: 23–24, 1986), motility (Nakamura, T. et al., Cancer Res., 57: 3305–3313, 1997) and differentiation (Kleinman, H. K. et al., Ann. NY Acad. Sci., 513: 134–145, 1987).

The present study showed the establishment of a novel 3D culture system in which human breast epithelial, breast fibroblasts and endothelial cells seeded as a mixed single cell suspension on a reconstituted basement membrane matrix, retained their inherent ability to segregate (or compartmentalize) and organize in a 3D manner with formation of a central stromal core composed of fibroblasts and functional endothelial cells from which, and around which, epithelial buds emerged. This structure resembles breast tissue in vivo where terminal ductules or acini are set within a rich and specialized stroma which define the lobular unit. This lobular connective tissue is usually loose, contains many capillaries and is sharply demarcated from the surrounding fat and more dense fibrous tissue of the "structural" vs. the "functional" part of the breast (Page, D. L. et al., 1987. Anatomy. In Diagnostic histopathology of the breast. Churchill Livingstone, p4–10).

The present co-culture assay system is physiologically relevant as it (1) permits the mammary epithelial cells to exhibit a homotypic affinity for themselves wherein they form an interface with an adjacent stromal core or compartment as observed in vivo, and
(2) facilitates an arrangement, observed in vivo, that is most suitable for functional paracrine interactions between epithelial-fibroblast and epithelial-endothelial cells.

Although the structural and functional organization observed in this system mimic several characteristics of the mammary gland, it is not so much representative of normal mammary gland morphology but rather of alterations occurring during early breast cancer.

The results show that the observed morphogenesis-inducing effects are selectively manifest by breast fibroblasts but not by normal lung or embryonal 3T3 fibroblasts or by soft tissue sarcoma-derived malignant mesenchymal cells. Even though the cultures are performed in Matrigel, a reconstituted basement membrane matrix containing a variety of ECM molecules (Li, M. L. et al., Proc. Natl. Acad. Sci. USA, 84: 136–140, 1987), induction of breast epithelial growth and morphogenesis appears to be mediated by ECM that is laid down by organ-specific mesenchyme.

The ability of normal fibroblasts to convert or revert malignant tumor lines such as basal cell carcinoma of skin (Cooper, M. et al., Cancer Res., 37: 2544–2552, 1977) and prostatic adenocarcinoma (Hayashi, N. et al., Cancer Res., 51: 4924–4930, 1991) into morphologically benign or biologically less aggressive cell populations has been demonstrated). The present findings show that while (i) normal breast tissue-derived fibroblasts obtained during reduction mammoplasty can inhibit or retard morphological transformation of both normal MCF10A epithelial cells and preneoplastic EIII8 breast epithelial cells,
(ii) tumor-derived breast fibroblasts can override or augment genetic constraints imposed by MCF10A or EIII8 cells, respectively, causing them to undergo ductal-alveolar morphogenesis.

This difference between normal and tumor-derived fibroblasts cannot be explained by variations in the "ages" of cells in culture as both sets of fibroblasts grew equally well at the passage numbers utilized for the experiments (four to six). Although the chronological ages of the donors differed (mean age 30 years for normal fibroblast donors and mean age 48 years for tumor-derived fibroblast donors), deviations in the activities of the fibroblasts cannot be ascribed to these age differences because the sample-to-sample variations in growth rates of both classes of fibroblasts far exceeded any age-associated differences.

Alterations in fibroblasts in the stroma immediately adjacent to transformed epithelial cells have been documented in several tumor systems (Chiquet-Ehrissmann, R. et al., Cell, 47: 131–139, 1986; Singer, C. et al., Cancer Res., 55: 2448–2454, 1995). Desmoplasia, a profound stromal response consisting of changes in cellular composition and ECM is known to occur in infiltrating ductal carcinoma (Tremblay, G., Exp. Mol. Pathol., 31: 248–260, 1979).

Differences in the activity of normal vs. tumor-derived fibroblasts may result from variations in establishment of reciprocal communication between epithelial and fibroblast compartments, which in turn could result from differences in molecular and/or cellular mechanisms that are responsible for the production and release of a number of soluble paracrine factors such as FGF(s) (Giri, D. et al., Clin. Cancer Res., 5: 1063–1071, 1999), TGF-β (Akhurst, R. J. et al., J. Pathol., 187: 82–90, 1999), insulin-like growth factors (IGFs) (Singer et al., supra), hepatocyte growth factor (Kasai, S. et al., Biochem. Biophys. Res. Commun., 228: 646–652, 1996), and/or ability to respond to epithelial-derived signals. Although potentially, any growth factor derived from breast fibroblasts may function as an important regulator of mammary tumor growth, IGFs, and IGF-II in particular, may play a key role in mediating breast tumor growth since IGF-II is expressed in the stroma of invasive breast cancers but not normal breast (Singer et al., supra), and in the stroma of N-nitrosomethylurea-induced rat mammary tumors (Manni, A, et al., Cancer Res., 54: 2934–2942, 1994).

While an important role for the stroma in mediating steroid action during growth and differentiation in many adult tissues has been proposed (Cunha, G. R. et al., supra), the present results show that normal fibroblasts have the ability to suppress $E_2$-induced growth of ER-positive EIII8 cells (see Example II and Shekhar et al., supra) whereas tumor-derived fibroblasts support $E_2$-induced growth of EIII8 cells. Although 10 nM $E_2$ was required to see a marginal increase in growth over that of control cultures, the $E_2$-induced effect was estrogen receptor-mediated because of the pure estrogen antagonist ICI 182,780 effectively blocked growth in both vehicle-treated and $E_2$-treated cultures. Therefore, it is concluded that the marginal induction of growth by exogenous estrogen may result from the presence of significant amounts of $E_2$ in the control cultures produced by tumor-derived fibroblasts via aromatase-mediated synthesis of estrogen (Pauley et al., supra; Reed, M. J. et al., Endocr. Rev., 18: 701–715, 1997; Sasano, H. et al., Endocr. Rev., 19: 593–607, 1998).

An alternate explanation of the differences between normal fibroblasts from reduction mammoplasty and tumor-derived fibroblasts may be the presence of genetic abnormalities in the benign/tumor fibroblasts. Moinfar et al (supra) reported frequent allelic loss in the stroma adjacent to breast cancer cells, ranging from 10 to 66.5 % for DCIS and from 20 to 75% for IDC, and the absence of LOH either in epithelial or stromal components in women without any breast disease. Thus, the genetic alterations in preneoplastic EIII8 cells (that are akin to many benign or early epithelial neoplasms), combined with the presence of a genetically altered stroma (such as that present in benign or malignant tumors of the breast), may explain the acute inductive responses observed in EIII8/12T or EIII8/38T co-cultures. Further support comes from the absence of similar effects in co-cultures of EIII8 with reduction mammoplasty fibroblasts cultures and the presence of such inductive responses in co-cultures of MCF10A with tumor fibroblasts.

Stromal-epithelial interaction has a fundamental role in normal duct development. Schor, A. M. et al. (Int. J Cancer, 59: 25–32, 1994) suggested that perturbations in epithelial-mesenchymal interactions caused by the presence of fibroblast subpopulations with "fetal-like" phenotypic properties in breast carcinomas and in histologically normal breast tissue adjacent to a carcinoma may significantly enhance susceptibility of epithelium to develop into cancer. Aberrations in stromal-epithelial interactions resulting from differences in production and release of growth factors, motility factors and/or ECM molecules that may potentially ensue from genetic alterations in the stromal compartment may thus play a vital role in the development and progression of human breast cancer.

It is interesting to note that the survival and function of endothelial cells are observed only in EIII8 co-cultures, seen as dramatic augmentation of proliferation and branching ductal-alveolar morphogenesis resulting from the addition of HUVECs to co-cultures of EIII8/12T or EIII8/38T. This was accompanied by increased invasion and degradation of the coincident ECM and upregulation of MMP-9. These finding are consistent with the results in Example II (and Shekhar et al., supra) that preneoplastic, but not normal, epithelial cells promote EC survival and function as the former cells respond to the presence of ECs with synthesis and release of the EC survival factor VEGF (14, 36, 37). It is concluded that tumor fibroblasts play an active role as a morphogenic and mitogenic inducer of epithelial cells, with a requirement for angiogenesis for further enhancement of tumor growth and progression The findings reported herein suggest that therapeutic targeting of stromal cells (in addition to cancer cells) may be beneficial because of their dominant capacity to modulate and control epithelial morphogenesis and mitogenesis. A therapy that inhibits tumor stroma may result in more effective tumor regression by depriving the tumor cells of an essential structural and functional support system.

The present invention provides a novel co-culture system that reconstitutes many of the functional interactions between breast epithelial and stromal cells. This system not only provides unique opportunities to characterize mechanisms regulating breast stromal-epithelial cell interactions but also has utility for the design and testing of effective therapeutic strategies.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A method for assaying a test agent for its activity in inhibiting molecular or cellular changes characteristic of preneoplastic breast disease in a three-dimensional in vitro culture system that serves as a model for preneoplastic breast disease, said method comprising:
 (a) providing said three-dimensional culture system, which comprise a co-culture of
  (i) preneoplastic breast epithelial cells,
  (ii) endothelial cells and
  (iii) breast fibroblasts on a reconstituted basement membrane in the presence of medium containing
   (1) effective concentrations of growth factors that act on said epithelial and endothelial cells, and
   (2) effective concentrations of an estrogen such that said cells undergo morphogenesis that results in the formation of a multicellular three dimensional network of branching ductal alveolar units in culture within about 3–7 days, (b) adding said test agent to said culture system for an interval sufficient for said agent to act upon said preneoplastic breast epithelial cells, said endothelial cells or said fibroblasts (c) to a parallel control culture, adding a negative control agent for said interval, which negative control agent does not prevent or inhibit said progression, (d) examining the cultures of (b) and (c), above, for
  i. formation of said branching ductal alveolar units by morphology; or
  ii. proliferation of cells; or
  iii. the presence in the culture medium of one or more secreted products of said cells wherein prevention or inhibition of said ductal alveolar unit formation, said proliferation or generation of said secreted products in cultures of (a) compared to (b), is indicative that said agent has said inhibitory activity.

2. The method of claim 1, additionally comprising use of a second parallel control culture to which is added a positive control agent known to inhibit said ductal alveolar unit formation, said proliferation or the generation of said secreted products when compared to said negative control agent.

3. The method of claim 1, wherein said assaying comprises, in step (c), examining said cultures morphologically for the presence or quantity of said branching ductal alveolar units.

4. The method of claim 1, wherein said assaying comprises, in step (c), measuring the proliferation of cells.

5. The method of claim 1, wherein said assaying comprises, in step (c), detecting the presence or measuring the amount of said secreted products in said culture medium.

6. The method of claim 4, wherein said proliferation is measured colorimetrically.

7. The method of claim 5 wherein said secreted product is a growth or angiogenic factor that is assayed by immunoreactivity in an immunoassay or by biological activity in a bioassay.

8. The method of claim 7 wherein said factor is VEGF.

9. The method of claim 7 wherein said factor is assayed for stimulation of proliferation of endothelial cells in culture.

10. The method of claim 7 wherein said factor is assayed for tube formation by endothelial cells in culture.

11. The method of claim 1, wherein said test agent inhibits or is suspected of inhibiting, proteolytic enzymes that are required for invasion and transformation to malignancy.

12. The method of claim 5 wherein said secreted product is a matrix metalloproteinase assayed by enzymatic activity on a specific substrate.

13. The method of claim 1 wherein said test agent induces or is suspected of inducing terminal differentiation of breast epithelial cells and thereby inhibits neoplastic conversion.

14. A method for testing an agent for its activity as an endothelial cell-specific or epithelial cell-specific factor active in promoting ductal-alveolar morphogenesis, angiogenesis and progression of preneoplastic breast epithelial cells to a malignant phenotype, comprising:

(a) providing a three-dimensional in vitro culture system that serves as a model for the development and progression of preneoplastic breast disease, said system comprising a co-culture of
  (i) preneoplastic breast epithelial cells,
  (ii) endothelial cells and
  (iii) breast fibroblasts on a reconstituted basement membrane in the presence of medium containing
    (1) effective concentrations of growth factors that act on said epithelial and endothelial cells, and,
    (2) effective concentrations of an estrogen such that said cells undergo morphogenesis that results in the formation of a multicellular three dimensional network of branching ductal alveolar units in culture within about 3–7 days.

(b) adding said test agent to said culture system for an interval sufficient for said agent to act upon said preneoplastic breast epithelial cells or said endothelial cells;

(c) to a parallel control culture, adding a negative control agent for said interval, which negative control agent does not promote ductal-alveolar morphogenesis, angiogenesis or progression of preneoplastic breast epithelial cell to a malignant phenotype;

(d) examining the cultures of (b) and (c), above, for
  i. formation of said branching ductal alveolar units by morphology; or
  ii. cellular changes corresponding to angiogenesis; or
  iii. progression of preneoplastic breast epithelial cells to a malignant phenotype, wherein promoting of said ductal alveolar unit formation, said cellular changes corresponding to angiogenesis, or said progression in cultures of (a) compared to (b), is indicative that said agent has said activity.

15. The method of claim 14, additionally comprising use of second parallel control culture to which is added a positive control agent known to promote ductal-alveolar morphogenesis, angiogenesis or progression of preneoplastic breast epithelial cells to a malignant phenotype when compared to said negative control agent.

16. The method of claim 1 wherein said growth factors that act on endothelial cells comprise one or more of epidermal growth factor, basic fibroblast growth factor and fibronectin, and said culture also comprises one or more of cholera toxin, insulin, and hydrocortisone.

17. The method of claim 14 wherein said growth factors that act on endothelial cells comprise one or more of epidermal growth factor, basic fibroblast growth factor and fibronectin, and said culture also comprises one or more of cholera toxin, insulin, and hydrocortisone.

18. The method of claim 1 wherein all of said cells are human cells.

19. The method of claim 14 wherein all of said cells are human cells.

20. The culture system of claim 1, wherein said epithelial cells are transformed by
(a) T24 Ha-ras cells; or
(b) cells derived from T24 Ha-ras cells by xenotransplantation in nude mice.

21. The culture system of claim 14 wherein said epithelial cells are transformed by
(a) T24 Ha-ras cells; or
(b) cells derived from T24 Ha-ras cells by xenotransplantation in nude mice.

22. The method of claim 20 wherein said epithelial cells are MCF10AT1 or MCF10AT1-EIII8 cells.

23. The method of claim 21 wherein said epithelial cells are MCF10AT1 or MCF10AT1-EIII8 cells.

24. The method of claim 1 wherein said endothelial cells are human umbilical vein endothelial cells.

25. The method of claim 14 wherein said endothelial cells are human umbilical vein endothelial cells.

26. The method of claim 1 wherein said medium is DMEM-F12 medium.

27. The method of claim 14 wherein said medium is DMEM-F12 medium.

28. The method of claims 26 wherein said medium is supplemented with 0.1 μg/ml cholera toxin, 10 μg/ml insulin, 0.5 μg/ml hydrocortisone and 0.02 μg/ml epidermal growth factor (EGF).

29. The method of claim 27 wherein said medium is supplemented with 0.1 μg/ml cholera toxin, 10 μg/ml insulin, 0.5 μg/ml hydrocortisone and 0.02 μg/ml epidermal growth factor (EGF).

30. The method of claim 1 wherein said estrogen is estradiol at a concentration between about 1 and 10 nM.

31. The method of claim 14 said estrogen is estradiol at a concentration between about 1 and 10 nM.

32. The method of claim 1, wherein as a result of secretion by said cells, said medium contains measurable concentrations or activities of one or more of interleukin-8, matrix metalloproteinase-2 and VEGF.

33. The method of claim 14, wherein as a result of secretion by said cells, said medium contains measurable concentrations or activities of one or more of interleukin-8, matrix metalloproteinase-2 and VEGF.

* * * * *